United States Patent
Higgins et al.

(10) Patent No.: US 11,685,957 B2
(45) Date of Patent: *Jun. 27, 2023

(54) MOLECULAR ASSAY METHODS

(71) Applicant: Gen-Probe Incorporated, San Diego, CA (US)

(72) Inventors: Scott Higgins, Bristol (GB); Mike Webb, Holcot (GB)

(73) Assignee: GEN-PROBE INCORPORATED, San Diego, CA (US)

( * ) Notice: Subject to any disclaimer, the term of this patent is extended or adjusted under 35 U.S.C. 154(b) by 288 days.

This patent is subject to a terminal disclaimer.

(21) Appl. No.: 17/199,683

(22) Filed: Mar. 12, 2021

(65) Prior Publication Data

US 2021/0198750 A1   Jul. 1, 2021

Related U.S. Application Data

(60) Continuation of application No. 16/785,837, filed on Feb. 10, 2020, now Pat. No. 10,995,375, which is a division of application No. 15/841,526, filed on Dec. 14, 2017, now Pat. No. 10,604,811, which is a division of application No. 14/356,368, filed as application No. PCT/US2012/063402 on Nov. 2, 2012, now Pat. No. 9,863,004.

(60) Provisional application No. 61/556,005, filed on Nov. 4, 2011.

(51) Int. Cl.
*C12Q 1/6886* (2018.01)
*C12Q 1/6848* (2018.01)
*C12Q 1/686* (2018.01)
*C12Q 1/6851* (2018.01)

(52) U.S. Cl.
CPC ........... *C12Q 1/6886* (2013.01); *C12Q 1/686* (2013.01); *C12Q 1/6848* (2013.01); *C12Q 1/6851* (2013.01); *C12Q 2545/101* (2013.01); *C12Q 2545/114* (2013.01); *C12Q 2600/112* (2013.01); *C12Q 2600/156* (2013.01); *C12Q 2600/16* (2013.01)

(58) Field of Classification Search
CPC ..................... C12Q 2545/101; C12Q 2600/16
See application file for complete search history.

(56) References Cited

U.S. PATENT DOCUMENTS

2010/0120035 A1* 5/2010 Ehrich .................. C12Q 1/686
435/6.12

OTHER PUBLICATIONS

Schweitzer, B. et al., Combining nucleic acid amplification and detection, Curr. Opinion in Biotechnol., vol. 12, pp. 21-27 (Year: 2001).*
Lang, A.H. et al., Optimized Allele-Specific Real-Time PCR Assays for the Detection of Common Mutations in KRAS and BRAF, J. Mol. Diagn., vol. 13, pp. 23-28 (Year: 2011).*

* cited by examiner

*Primary Examiner* — Teresa E Strzelecka
(74) *Attorney, Agent, or Firm* — Nicholas V. Sherbina; Jeffrey E. Landes

(57) ABSTRACT

Methods, kits, and compositions for evaluating the quality of nucleic acids within a biological sample for analysis in a molecular assay are provided.

20 Claims, 16 Drawing Sheets
Specification includes a Sequence Listing.

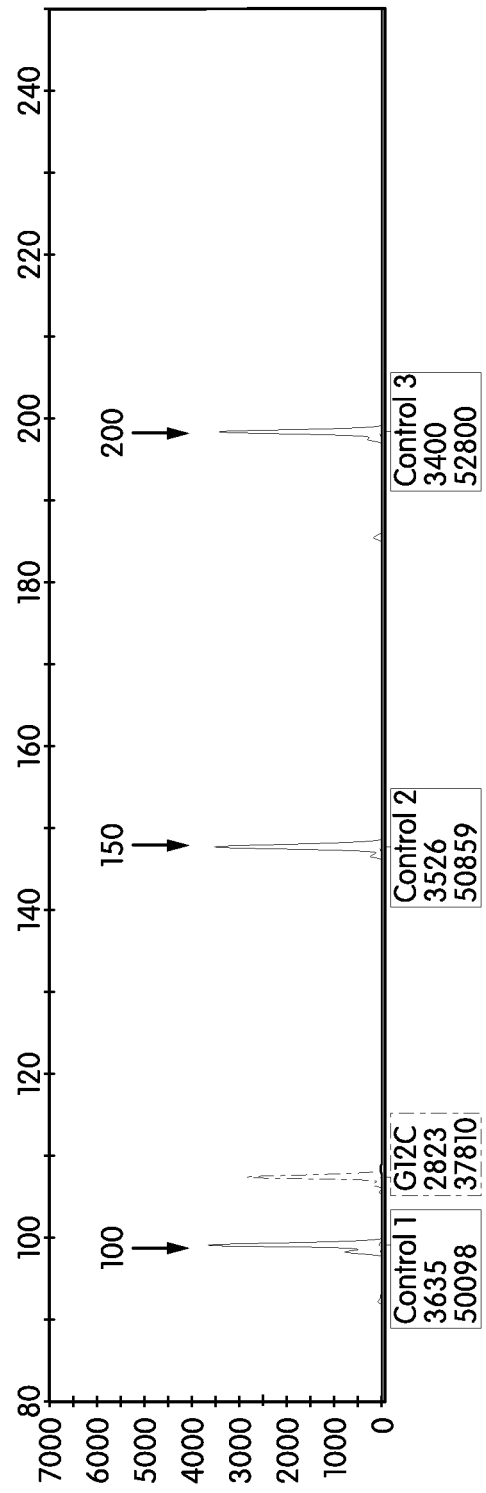
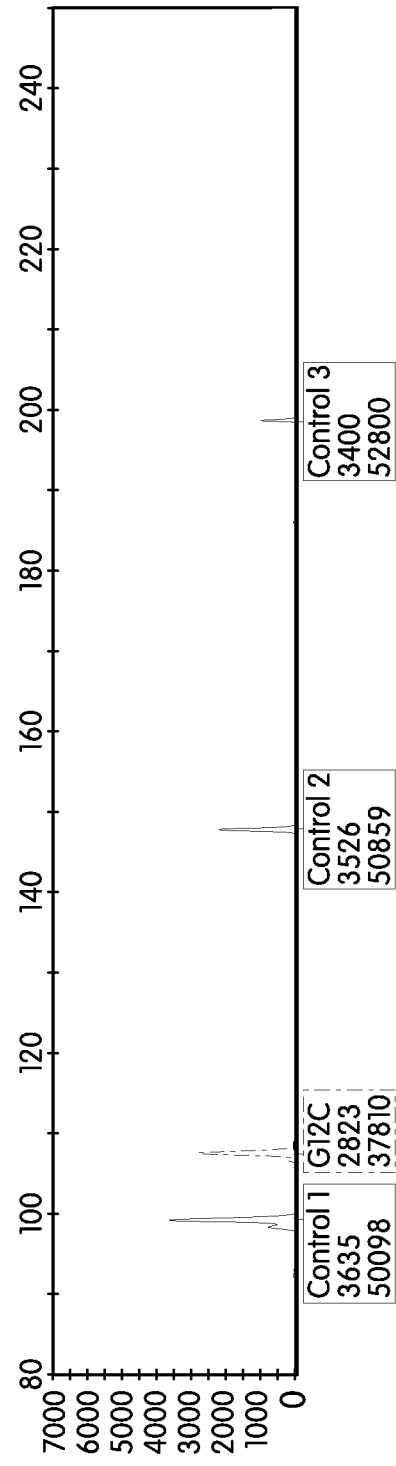
FIG. 1A
FIG. 1B

SEQ ID NO:9
(nt residues 1-1560)

```
   1 cgcaagtccc ccaccgttc agcgcaaccg ggccctccca gcccgcgc cgtccccctc
  61 cccgccctg gtctctttc cgcgctgcgg tcagcctgcg cgtcccacag agaggccag
 121 aggtggaaac gcagaaaacc aaaccaggac tatcagagat tgcccggaga gggatgcga
 181 cccctcccca ggtcgcagcg acggcgcacg caagggtcac ggagcatgcg ttggctaccc
 241 ggcgccgggg accgctgcca ccccgcccc cgcagcgccc cgtccttccg cagcccaacc
 301 gcctcttccc gccccgcccc atcccgccca cgggctccag tgggcgggac cagaggagtc
 361 ccgcgttcgg ggagtatgtc aaggccgtga cccgtgtatt attgtccgag tggccggaac
 421 gggagccaac atggcagcgg ggttcgggcg atgctgcagg tgttcttac aggtcctgag
 481 aagtatttct cgttttcatt ggagatcaca gcatacaaaa gccaatcgac aacgtgaacc
 541 aggattagga tttagttttg agttcaccga acagcagaaa gaatttcaag ctactgctcg
 601 taaatttgcc agagaggaaa tcatcccagt ggctgcagaa tatgataaaa ctggtgaata
 661 tccagtcccc ctaattagaa gagcctggga acttggttta atgaacacac acattccaga
 721 gaactgtgga ggtcttggac ttgaactttt tgatgcttgt ttaattagtg aagaattggc
 781 ttatggatgt acagggttc agactgctat tgaaggaaat tctttgggc aaatgcctat
 841 tattattgct ggaaatgatc aacaaaagaa gaagtatttg gggagaatga ctgaggagcc
 901 attgatgtgt gcttattgtg taacagaacc tggagcaggc tctgatgtag ctggtataaa
 961 gaccaaagca gaaaagaaag gagatgagta tattattaat ggtcagaaga tgtggataac
1021 caacgggaga aaagctaatt ggtattttt attggcacgt tctgatccag atcctaaagc
1081 tcctgctaat aaagcctta ctgattcat tgtggaagca gatacccag gaattcagat
1141 tgggagaaag gaattaaaca tggccagcg atgttcagat actagaggaa ttgtcttcga
1201 agatgtgaaa gtgcctaaag aaaatgtttt aattggtgac ggagctggtt tcaaagttgc
1261 aatgggagct tttgataaaa ccagacctgt agtagctgct ggtgctgttg gattagcaca
1321 aagagctttg gatgaagcta cctgaaagg aaaactttcg gaaagtact
1381 tgtagcac caagcaatat catttatgct ggctgaaatg gcaatgaaag ttgaactagc
1441 tagaatgagt taccagagag cagcttggga ggttgattct ggtcgtcgaa atacctatta
1501 tgcttctatt gcaaaggcat ttgctggaga tattgcaaat cagttagcta ctgatgctgt
```

FIG. 9A

SEQ ID NO:9
(nt residues 1561-2627)

```
1561 gcagatactt ggaggcaatg gatttaatac agaatatcct gtagaaaaac taatgaggga
1621 tgccaaaatc tatcagattt atgaaggtac ttcacaaatt caaagactta ttgtagcccg
1681 tgaacacatt gacaagtaca aaaattaaaa aaattactgt agaaatattg aataactaga
1741 acacaagcca ctgtttcagc tccagaaaaa agaaagggct ttaacgtttt ttccagtgaa
1801 aacaaatcct cttatattaa atctaagcaa ctgcttatta tagtagttta tacttttgct
1861 taactctgtt atgtctctta agcaggtttg gttttattta aaatgatgtg tttttcttag
1921 taccacttta cttgaattac attaacctag aaaactacat aggttatttt gatctcttaa
1981 gattaatgta gcagaaattt cttggaattt tatttttgta atgacagaaa agtgggctta
2041 gaaagtattc aagatgttac aaaatttaca tttagaaaat attgtagtat ttgaatactg
2101 tcaacttgac agtaactttg tagacttaat ggtattatta aagttctttt tattgcagtt
2161 tggaaagcat ttgtgaaact ttctgtttgg cacagaaaca gtcaaaattt tgacattcat
2221 attctcctat tttacagcta caagaacttt cttgaaaatc ttatttaatt ctgagcccat
2281 atttcactta ccttatttaa aataaatcaa taaagcttgc cttaaattat ttttatatga
2341 ctgttggtct ctaggtagcc tttggtctat tgtacacaat ctcatttcat atgtttgcat
2401 tttggcaaag aacttaataa aattgttcag tgcttattat catatctttc tgtattttt
2461 ccaggaaatt tcattacttc gtgtaatagt gtatattcct tgtattact atgatgaaaa
2521 aaggtcgttt taattttgaa ttgaataaag ttacctgttc atttttatt agatatttta
2581 aagacttcag aaaatataaa tatgaaataa tttaaaaaaa aaaaaaa
```

FIG. 9B

SEQUENCE LISTING

```
<160> NUMBER OF SEQ ID NOS: 9

<210> SEQ ID NO 1
<211> LENGTH: 32
<212> TYPE: DNA
<213> ORGANISM: Artificial Sequence
<220> FEATURE:
<223> OTHER INFORMATION: Synthetic

<400> SEQUENCE: 1
gtacttcaca aattcaaaga cttattgtat cc                                      32

<210> SEQ ID NO 2
<211> LENGTH: 32
<212> TYPE: DNA
<213> ORGANISM: Artificial Sequence
<220> FEATURE:
<223> OTHER INFORMATION: Synthetic

<400> SEQUENCE: 2
gtacttcaca aattcaaaga cttattgtag cc                                      32

<210> SEQ ID NO 3
<211> LENGTH: 33
<212> TYPE: DNA
<213> ORGANISM: Artificial Sequence
<220> FEATURE:
<223> OTHER INFORMATION: Synthetic

<400> SEQUENCE: 3
tcaatatttc tacagtaatt tttttaattt ttg                                     33

<210> SEQ ID NO 4
<211> LENGTH: 39
<212> TYPE: DNA
<213> ORGANISM: Artificial Sequence
```

```
<220> FEATURE:
<223> OTHER INFORMATION: Synthetic

<400> SEQUENCE: 4
tcaatatttc tacagtaatt tttttaattt ttgtacttg                                39

<210> SEQ ID NO 5
<211> LENGTH: 38
<212> TYPE: DNA
<213> ORGANISM: Artificial Sequence
<220> FEATURE:
<223> OTHER INFORMATION: Synthetic

<400> SEQUENCE: 5
cttgtgttct agttattcaa tatttctaca gtaatttt                                 38

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
ctggaaaaaa cgttaaagcc ctttct                                             26

<210> SEQ ID NO 7
<211> LENGTH: 39
<212> TYPE: DNA
<213> ORGANISM: Artificial Sequence
<220> FEATURE:
<223> OTHER INFORMATION: Synthetic

<400> SEQUENCE: 7
ctactataat aggcagttgc ttagatttaa tataagagg                                39

<210> SEQ ID NO 8
<211> LENGTH: 42
<212> TYPE: DNA
<213> ORGANISM: Artificial Sequence
<220> FEATURE:
<223> OTHER INFORMATION: Synthetic

<400> SEQUENCE: 8
tctaggttaa tgtaattcaa gtaaagtggt actaaagaaa ac                            42

<210> SEQ ID NO 9
<211> LENGTH: 2627
<212> TYPE: DNA
<213> ORGANISM: Homo sapiens

<400> SEQUENCE: 9
cgcaagtccc cccaccgttc agcgcaaccg ggccctccca gccccgccgc cgtccccctc         60
ccccgccctg gctctctttc cgcgctgcgg tcagcctcgg cgtcccacag agagggccag        120
aggtggaaac gcagaaaacc aaaccaggac tatcagagat tgcccggaga ggggatgcga        180
cccctcccca ggtcgcagcg acggcgcacg caagggtcac ggagcatgcg ttggctaccc        240
ggcgccgggg accgctgcca ccccgcctag cgcagcgccc cgtccttccg cagcccaacc        300
gcctcttccc gccccgcccc atcccgccca cgggctccag tgggcgggac cagaggagtc        360
ccgcgttcgg ggagtatgtc aaggccgtga cccgtgtatt attgtccgag tggccggaac        420
gggagccaac atggcagcgg ggttcgggcg atgctgcagg tgttctttac aggtcctgag        480
```

```
aagtatttct cgttttcatt ggagatcaca gcatacaaaa gccaatcgac aacgtgaacc    540
aggattagga tttagttttg agttcaccga acagcagaaa gaatttcaag ctactgctcg    600
taaatttgcc agagaggaaa tcatcccagt ggctgcagaa tatgataaaa ctggtgaata    660
tccagtcccc ctaattagaa gagcctggga acttggttta atgaacacac acattccaga    720
gaactgtgga ggtcttggac ttggaacttt tgatgcttgt ttaattagtg aagaattggc    780
ttatggatgt acaggggttc agactgctat tgaaggaaat tctttggggc aaatgcctat    840
tattattgct ggaaatgatc aacaaaagaa gaagtatttg gggagaatga ctgaggagcc    900
attgatgtgt gcttattgtg taacagaacc tggagcaggc tctgatgtag ctggtataaa    960
gaccaaagca gaaaagaaag gagatgagta tattattaat ggtcagaaga tgtggataac   1020
caacggagga aaagctaatt ggtattttt attggcacgt tctgatccag atcctaaagc   1080
tcctgctaat aaagccttta ctggattcat tgtggaagca gatacccag gaattcagat   1140
tgggagaaag gaattaaaca tgggccagcg atgttcagat actagaggaa ttgtcttcga   1200
agatgtgaaa gtgcctaaag aaaatgtttt aattggtgac ggagctggtt tcaaagttgc   1260
aatgggagct tttgataaaa ccagacctgt agtagctgct ggtgctgttg gattagcaca   1320
aagagctttg gatgaagcta ccaagtatgc cctggaaagg aaaactttcg gaaagctact   1380
tgtagagcac caagcaatat catttatgct ggctgaaatg gcaatgaaag ttgaactagc   1440
tagaatgagt taccagagag cagcttggga ggttgattct ggtcgtcgaa atacctatta   1500
tgcttctatt gcaaaggcat ttgctggaga tattgcaaat cagttagcta ctgatgctgt   1560
gcagatactt ggaggcaatg gatttaatac agaatatcct gtagaaaaac taatgaggga   1620
tgccaaaatc tatcagattt atgaaggtac ttcacaaatt caaagactta ttgtagcccg   1680
tgaacacatt gacaagtaca aaaattaaaa aaattactgt agaaatattg aataactaga   1740
acacaagcca ctgtttcagc tccagaaaaa agaaagggct ttaacgtttt ttccagtgaa   1800
aacaaatcct cttatattaa atctaagcaa ctgcttatta tagtagttta acttttgct   1860
taactctgtt atgtctctta agcaggtttg gttttttatta aaatgatgtg ttttctttag   1920
taccacttta cttgaattac attaacctag aaaactacat aggttatttt gatctcttaa   1980
gattaatgta gcagaaattt cttggaattt tatttttgta atgacagaaa agtgggctta   2040
gaaagtattc aagatgttac aaaatttaca tttagaaaat attgtagtat ttgaatactg   2100
tcaacttgac agtaactttg tagacttaat ggtattatta aagttctttt tattgcagtt   2160
tggaaagcat ttgtgaaact ttctgtttgg cacagaaaca gtcaaaattt tgacattcat   2220
attctcctat tttacagcta caagaacttt cttgaaaatc ttatttaatt ctgagcccat   2280
atttcactta ccttatttaa aataaatcaa taaagcttgc cttaaattat tttatatga   2340
ctgttggtct ctaggtagcc tttggtctat tgtacacaat ctcatttcat atgtttgcat   2400
tttggcaaag aacttaataa aattgttcag tgcttattat catatctttc tgtattttt   2460
ccaggaaatt tcattacttc gtgtaatagt gtatatttct tgtatttact atgatgaaaa   2520
aaggtcgttt taattttgaa ttgaataaag ttacctgttc attttttatt agatatttta   2580
aagacttcag aaaatataaa tatgaaataa tttaaaaaaa aaaaaaa                 2627
```

MOLECULAR ASSAY METHODS

CROSS-REFERENCE TO RELATED APPLICATIONS

This application is a continuation U.S. application Ser. No. 16/785,837, filed Feb. 10, 2020, now issued as U.S. Pat. No. 10,995,375, which is a divisional of U.S. application Ser. No. 15/841,526, filed Dec. 14, 2017, now issued as U.S. Pat. No. 10,604,811, which is a divisional of U.S. application Ser. No. 14/356,368, filed May 5, 2014, now issued as U.S. Pat. No. 9,863,004, which is a national stage entry of International Application No. PCT/US2012/063402, filed Nov. 2, 2012, which claims the benefit of U.S. Provisional Application No. 61/556,005, filed Nov. 4, 2011, the contents of each of which applications is hereby incorporated by reference herein.

REFERENCE TO SEQUENCE LISTING

The instant application contains a Sequence Listing which has been submitted in ASCII format via EFS-Web and is hereby incorporated by reference in its entirety. Said ASCII Copy, created on Feb. 7, 2021, is named "GP281_04CN1_SeqList_ST25" and is 5,335 bytes in size.

FIELD OF THE INVENTION

The present invention relates to control reagents for evaluating biological samples.

BACKGROUND

Access to and use of human specimens is an essential part of the cancer research and drug discovery infrastructure, enabling researchers to, inter alia, correlate gene mutations/polymorphisms with particular cancers, identify drug targets, develop therapeutic compounds, guide therapy decisions, and understand drug metabolism. Research using human specimens can help predict drug response and toxicity, and clinical outcome. Many different types of biological specimens are required to support these studies: normal and malignant tissues, blood, blood products, other bodily fluids, as well as proteins and nucleic acids that can be extracted from them.

Formalin-fixed, paraffin-embedded (FFPE) tissue, which is one common method of preserving specimens, is a frequent source of biological specimens. Formaldehyde fixation, however, causes cross-linking between nucleic acids and proteins, the reversal of which leads to fragmentation of DNA and RNA. And, the paraffin-embedded tissue sections require de-waxing to allow penetration by aqueous solutions prior to analysis of nucleic acids.

For example, in one extraction procedure a razor blade is used to scrape FFPE sections, which are then transferred into microfuge tubes for processing. The traditional method of paraffin removal involves organic extractions using xylene and graded alcohols. This procedure is time-consuming, cumbersome, and requires special handling, as xylene is a highly toxic chemical that emits noxious fumes.

Phase extraction de-waxing protocols are time consuming and laborious. And, the repeated handling, aspirations and tube transfers can result in non-quantitative harvests of the nucleic acids. Moreover, repeated vortexing of the sample and exposure to harsh solvents can cause additional sample degradation. Commercial kits are available that optimize the nucleic acid extraction process but the resulting quality and quantity of nucleic acid recovered from FFPE tissues is variable.

Problems exist in the quantitation of nucleic acids from preserved clinical specimens such as FFPE tissues. Extracted nucleic acid quality and quantity is often affected by both sample collection and extraction procedures due to degradation and fragmentation. This can compromise, for example, the ability to measure the extracted nucleic acids. Qualitative and quantitative assay errors often result when these extracts are evaluated by standard analytical techniques. Moreover, incomplete extractions can introduce error into calculations, such as mRNA copy number determinations.

A variety of methods exist for attempting to assess the quantity and quality of extracted nucleic acids. For example, 260 nm/280 nm absorbance by spectrophotometry can assess high molecular weight (intact) genomic DNA. But nucleic acid fragmentation can result in highly erroneous results and an overestimation of nucleic acid amounts. The use of intercalating dyes is also widely used, however, the accuracy of assays based on these dyes are significantly impacted by an over-abundance of small nucleic acid fragments in degraded sample.

Sensitivity of detection of a genetic variant is dependent upon the quantity and quality of nucleic acid available for analysis. Although existing methods that are used to determine nucleic acid quantity and quality are useful in limited circumstances, they generally involve additional testing prior to genetic analysis of a sample. A simple method to evaluate the quantity and quality of DNA or RNA simultaneously with the genetic analysis is therefore needed.

SUMMARY OF THE INVENTION

A kit is provided for evaluating a biological sample containing potentially degraded DNA, comprising a control reagent and a target amplification reagent, wherein the control amplification reagent comprises one or more pairs of amplification oligonucleotides capable of amplifying a medium chain acyl-coenzyme A dehydrogenase (MCAD) nucleic acid molecule or a complement thereof, and wherein the target amplification reagent comprises one or more pairs of amplification oligonucleotides capable of amplifying a non-MCAD target gene of interest or a complement thereof. Frequently, one or more of the amplification oligonucleotides is/are labeled. Also frequently, the biological sample comprises a tissue sample, which often comprises a formalin-fixed paraffin-embedded (FFPE) tissue sample.

In certain embodiments two or more pairs of amplification oligonucleotides are provided that are capable of amplifying an MCAD nucleic acid molecule or a complement thereof. In frequent embodiments three or more pairs of amplification oligonucleotides are provided that are capable of amplifying an MCAD nucleic acid molecule or a complement thereof. In frequent embodiments each of the two or more pairs of amplification oligonucleotides comprises a sense amplification oligonucleotide and an antisense oligonucleotide, and wherein the sense amplification oligonucleotide of each of the two or more pairs of amplification oligonucleotides comprises the same oligonucleotide sequence. Also frequently, each of the two or more pairs of amplification oligonucleotides comprises a sense amplification oligonucleotide and an antisense oligonucleotide, and wherein the antisense amplification oligonucleotide of each of the two or more pairs of amplification oligonucleotides comprises the same oligonucleotide sequence. Often, each pair of amplification oligonucleotides is capable of amplifying a region of the MCAD nucleic acid molecule to produce an MCAD amplicon, and wherein each MCAD amplicon produced by each pair of amplification oligonucleotides is detectably distinguishable from the MCAD amplicon produced by each other pair of amplification oligonucleotides.

In frequent embodiments each MCAD amplicon produced by each pair of amplification oligonucleotides is detectably distinguishable from the MCAD amplicon produced by each other pair of amplification oligonucleotides on the length of each MCAD amplicon.

Methods for evaluating the quality of a biological sample are also provided, comprising: (a) contacting a nucleic acid molecule obtained from a tissue sample with a control amplification reagent to form a reaction mixture, wherein the nucleic acid molecule comprises a highly conserved region of a control nucleic acid; (b) subjecting the reaction mixture to amplification conditions to produce an amplification mixture, whereby two or more portions of the highly conserved region of the control nucleic acid are amplified to produce two or more detectably distinguishable control amplicons, each having a different length, wherein the two or more different length control amplicons form a size control ladder comprised of amplicons of increasing length; and (c) evaluating the amplification mixture to detect the length and amount of each control amplicon, wherein the biological sample is determined to contain degraded nucleic acid molecules that may adversely impact molecular analysis of the biological sample if: (1) the amount detected of each of the two or more control amplicons is smaller than the amount detected of each of the two or more control amplicons in a comparative control sample; (2) the amount detected of each of the two or more control amplicons in the size control ladder decreases as the length of each control amplicon in the size control ladder increases; or (3) one or more of the control amplicons are undetectable after production of the amplification mixture. Frequently, the biological sample comprises a tissue sample such as an FFPE tissue sample.

In certain frequent embodiments the control nucleic acid comprises MCAD.

Frequently, the results of the method are utilized to evaluate a molecular assay involving the biological sample. Also frequently the results of the method are utilized to reject the results of a molecular assay involving the biological sample.

Methods of conducting an amplification assay are also provided, comprising: (a) contacting a biological sample with a control amplification reagent and a target amplification reagent to form a reaction mixture, wherein the control amplification reagent is capable of taking part in a nucleic acid amplification reaction involving a highly conserved region of a control nucleic acid or a portion thereof, if present in the biological sample, and wherein the target amplification reagent is capable of taking part in a nucleic acid amplification reaction involving a target nucleic acid or a portion thereof, if present in the biological sample; (b) subjecting the reaction mixture to amplification conditions to produce an amplification mixture, whereby a portion of the highly conserved region of the control nucleic acid and the target nucleic acid or portion thereof, if present, are amplified to produce a detectable control amplicon and a detectable target amplicon; (c) evaluating the amplification mixture to detect the control amplicon and the target amplicon; and (d) comparing the detected control amplicon with the detected target amplicon to evaluate the amount and quality of the target nucleic acid or portion thereof and/or the highly conserved region of the control nucleic acid or portion thereof, present in the biological sample. In certain embodiments the target nucleic acid and/or control nucleic acid comprises genomic DNA.

In certain frequent embodiments the control nucleic acid comprises MCAD.

Also frequently, the control amplification reagent comprises amplification oligonucleotides for use in producing two or more detectably distinguishable control amplicons, each having a different length, wherein the two or more different length control amplicons form a size control ladder comprised of amplicons of increasing length. Often, the target amplification reagent comprises amplification oligonucleotides for use in producing one or more detectable amplicons for each target nucleic acid.

The target nucleic acid reagent of the present kits and methods is not limited. However, often the target nucleic acid reagent comprises a reagent specific for wild-type or mutant v-Raf murine sarcoma viral oncogene homolog B1 (BRAF), V-Ki-ras2 Kirsten rat sarcoma viral oncogene homolog (KRAS), epidermal growth factor receptor (EGFR), phosphatidylinositol 3-kinase (PIK3CA), phosphatase and tensin homolog (PTEN), v-akt murine thymoma viral oncogene homolog (AKT), anaplastic lymphoma kinase (ALK), mast/stem cell growth factor receptor (c-Kit), neuroblastoma RAS viral oncogene homolog (NRAS), met proto-oncogene hepatocyte growth factor receptor (c-Met), prostate cancer gene 3 (PCA3), prostate specific membrane antigen (PSMA), prostate specific antigen (PSA), tumor protein 53 (TP53), Echinoderm microtubule-associated protein-like 4 (EML4), EML4-ALK fusions, androgen regulated gene-ETS family member gene fusions, RAF gene fusions, breakpoint cluster region—V-abl Abelson murine leukemia viral oncogene homolog 1 fusions (BCR-Abl), cytochrome P450 2D6 (CYP2D6), cytochrome P450 2C19 (CYP2C19), cytochrome P450 2C9 (CYP2C9), vitamin K epoxide reductase complex subunit 1 (VKORC1), thiopurine methyltransferase (TMPT), bilirubin UDP-glucuronosyltransferase isozyme 1 (UGT1A1), and/or ATP-binding cassette sub-family B member 1 (ABCB1), or combinations thereof.

BRIEF DESCRIPTION OF THE DRAWINGS

FIG. 1A, FIG. 1B, FIG. 1C depict exemplary results of an assay of good quality (FIG. 1A), acceptable quality (FIG. 1B), and very degraded DNA (FIG. 1C) using control reagents of the present disclosure. The X-coordinate depicts amplicon size, and the Y-coordinate depicts fluorescence intensity in RFUs.

The X-coordinate depicts amplicon size, and the Y-coordinate depicts fluorescence intensity in RFUs.

Figure 6:
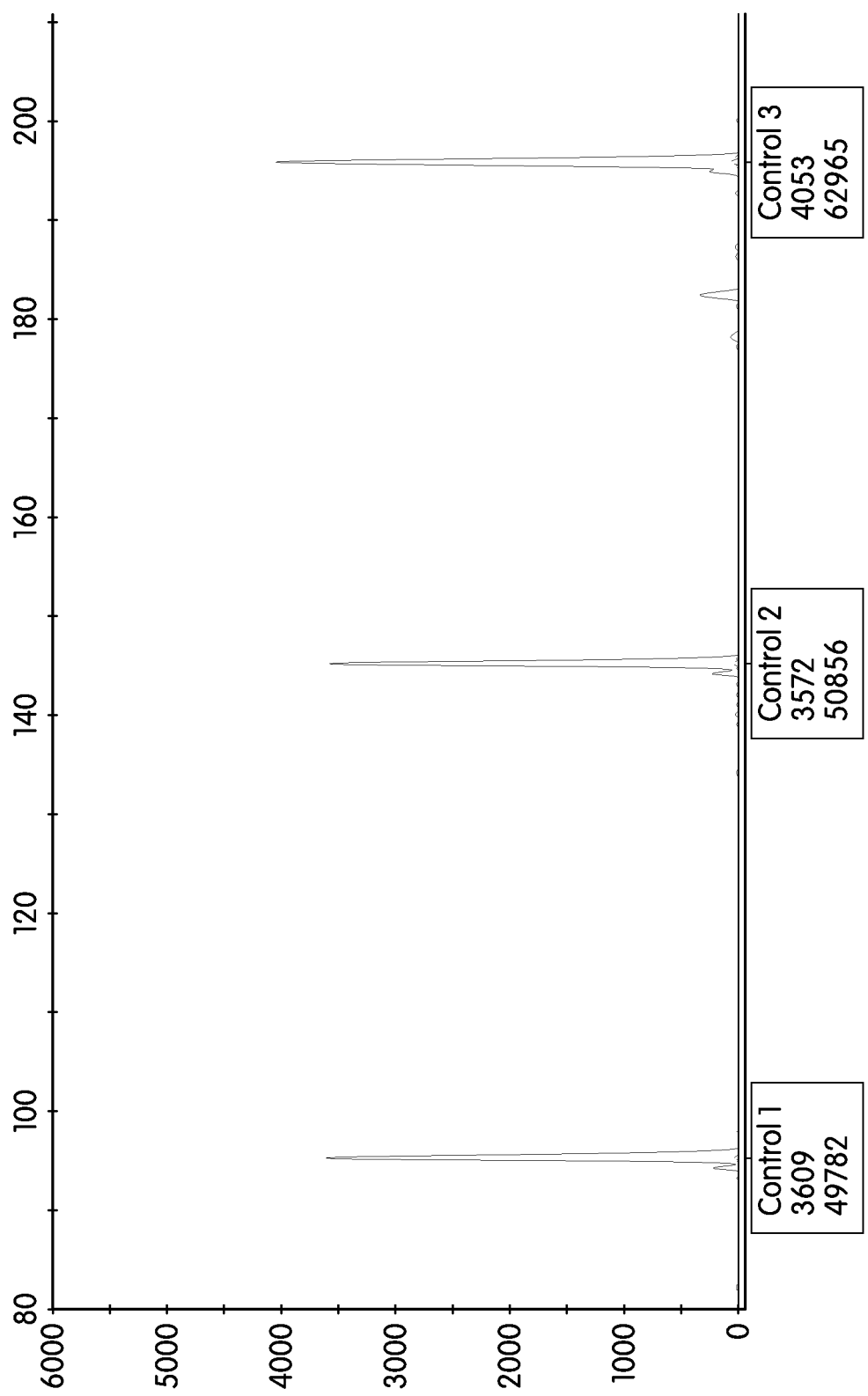

FIG. 6 depicts exemplary results of an assay of good quality and sufficient amounts of DNA using control reagents of the present disclosure. The X-coordinate depicts amplicon size, and the Y-coordinate depicts fluorescence intensity in RFUs.

Figure 7:
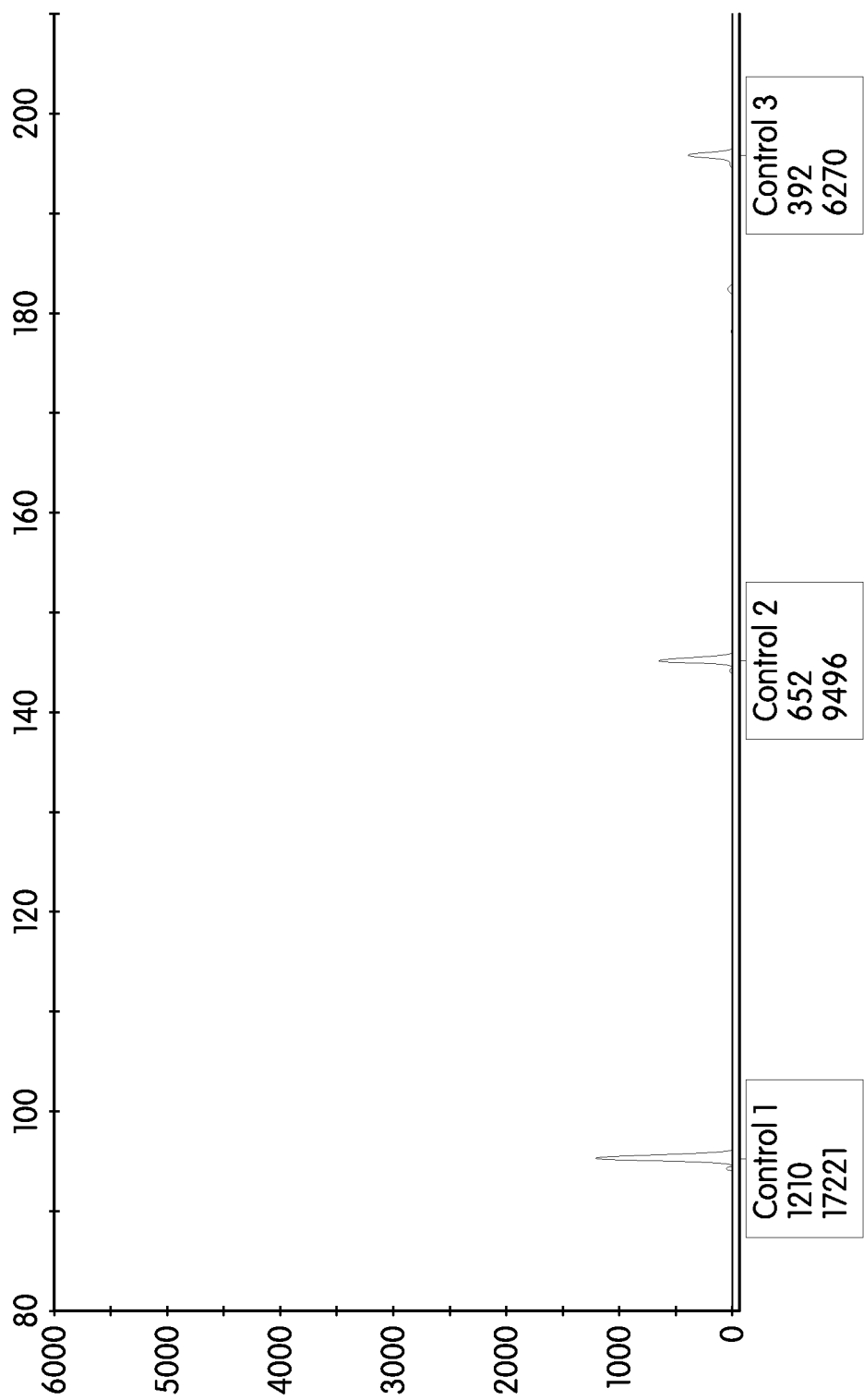

FIG. 7 depicts exemplary results of an assay of degraded and lower amounts of DNA using control reagents of the present disclosure. The X-coordinate depicts amplicon size, and the Y-coordinate depicts fluorescence intensity in RFUs.

Figure 8:
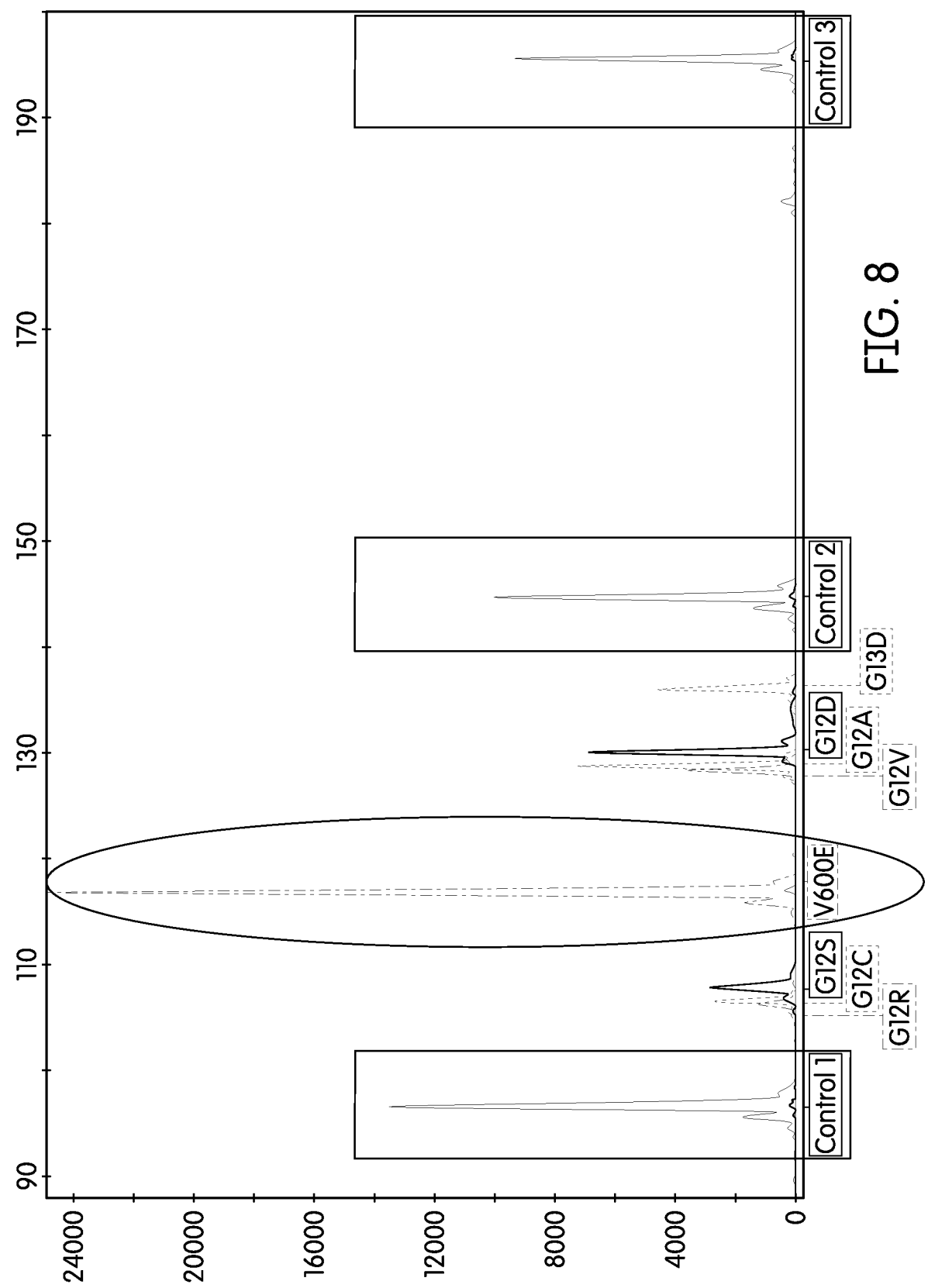

FIG. 8 depicts exemplary results of an assay identifying multiple mutant DNA amplicons in addition to control DNA. The X-coordinate depicts amplicon size, and the Y-coordinate depicts fluorescence intensity in RFUs.

FIG. 9A and FIG. 9B depict the mRNA sequence of Medium Chain Acyl-CoA Dehydrogenase gene or "MCAD," GenBank Accession Number NM_001127328.

DETAILED DESCRIPTION OF THE INVENTION

Unless defined otherwise, all terms of art, notations and other scientific terms or terminology used herein have the same meaning as is commonly understood by one of ordinary skill in the art to which this disclosure belongs. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

As used herein, "a" or "an" means "at least one" or "one or more."

The term "about" is used herein to mean approximately, roughly, around, or in the region of. When the term "about" is used in conjunction with a numerical range, it modifies that range by extending the boundaries above and below the values set forth. In general, the term "about" is used herein to modify a numerical value above and below the stated value by a deviation of 20 percent.

As used herein, the word "or" means any one member of a particular list and also includes any combination of members of that list.

As used herein, the terms "detect," "detecting" or "detection" may describe either the general act of discovering or discerning or the specific observation of a composition, whether it is labeled or otherwise. In frequent embodiments, the detection process involves evaluating something (e.g., a sample, a reaction product, etc.) for the presence of a detectable signal (e.g., fluorescence) attributable to the presence of a particular analyte. A particular detectable signal level or strength (e.g., strong or large relative fluorescence levels) often denotes a particular pre-determined characteristic of the analyte such as analyte amount, analyte size, sample quality, etc.

"Nucleic acid" or "nucleic acid molecule" refers to a multimeric compound comprising nucleotides or analogs which have nitrogenous heterocyclic bases or base analogs linked together to form a polynucleotide, including conventional RNA, DNA, mixed RNA-DNA, and polymers that are analogs thereof. A nucleic acid "backbone" may be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid may be ribose, deoxyribose, or similar compounds with substitutions, e.g., 2' methoxy or 2' halide substitutions. Nitrogenous bases may be conventional bases (A, G, C, T, U), analogs thereof (e.g., inosine or others; see THE BIOCHEMISTRY OF THE NUCLEIC ACIDS 5-36 (Adams et al., ed., $11^{th}$ ed., 1992), derivatives of purines or pyrimidines (e.g., $N^4$-methyl deoxyguanosine, deaza- or aza-purines, deaza- or aza-pyrimidines, pyrimidine bases with substituent groups at the 5 or 6 position, purine bases with a substituent at the 2, 6 or 8 positions, 2-amino-6-methylaminopurine, O.sup.6-methyl-guanine, 4-thio-pyrimidines, 4-amino-pyrimidines, 4-dimethylhydrazine-pyrimidines, and O.sup.4-alkyl-pyrimidines; U.S. Pat. No. 5,378,825 and PCT No. WO 93/13121). Nucleic acids may include one or more "abasic" residues where the backbone includes no nitrogenous base for one or more positions (U.S. Pat. No. 5,585,481). A nucleic acid may include only conventional RNA or DNA sugars, bases and linkages, or may include both conventional components and substitutions (e.g., conventional bases with 2' methoxy linkages, or polymers containing both conventional bases and analogs). The term includes "locked nucleic acid" (LNA), an analogue containing one or more LNA nucleotide monomers with a bicyclic furanose unit locked in an RNA mimicking sugar conformation, which enhance hybridization affinity for complementary RNA and DNA sequences (Vester et al., Biochemistry, 2004, 43(42):13233-41). Embodiments of oligomers that may affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates).

"Oligomer" or "oligonucleotide" refers to a nucleic acid of generally less than 1,000 nucleotides (nt), including those in a size range having a lower limit of about 2 to 5 nt and an upper limit of about 500 to 900 nt. Some preferred embodiments are oligomers in a size range with a lower limit of about 5 to 15 nt and an upper limit of about 50 to 600 nt, and other preferred embodiments are in a size range with a lower limit of about 10 to 20 nt and an upper limit of about 22 to 100 nt. Oligomers may be purified from naturally occurring sources, but preferably are synthesized by using any well-known enzymatic or chemical method. Oligomers may be referred to by functional names (e.g., capture probe, primer or promoter primer) which are understood to refer to oligomers.

The term "gene" refers to a nucleic acid molecule that comprises non-coding and coding sequences, or just coding sequences necessary for the production of a polypeptide, precursor, or RNA. The polypeptide can be encoded by a full length coding sequence or by any portion of the coding sequence. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences."

A "sample" or "specimen" refers to any composition in which a control or target nucleic acid may exist as part of a mixture of components, e.g., in water or environmental samples, food stuffs, materials collected for forensic analysis, or biopsy samples for diagnostic testing. "Biological sample" refers to any tissue or material derived from a living or dead organism which may contain a target nucleic acid, including, e.g., cells, tissues, lysates made from cells or tissues, sputum, peripheral blood, plasma, serum, cervical swab samples, biopsy tissues (e.g., lymph nodes), respiratory tissue or exudates, gastrointestinal tissue, urine, feces, semen, or other fluids or materials. A sample may be treated to physically disrupt tissue and/or cell structure to release intracellular components into a solution which may contain enzymes, buffers, salts, detergents and other compounds, such as are used to prepare a sample for analysis by using standard methods. The sample may require preliminary processing designed to purify, isolate, and/or enrich the sample for the target(s) or cells that contain the target(s). A variety of techniques known to those of ordinary skill in the art may be used for this purpose, including but not limited to: centrifugation; immunocapture; cell lysis; and, nucleic acid target capture (See, e.g., EP Pat. No. 1409727, incorporated herein by reference).

As used herein, the "Medium Chain Acyl-CoA Dehydrogenase" gene or "MCAD" refers to the gene referenced in GenBank Accession Number NM_001127328. The MCAD gene maps to chromosome 1p31, comprises 12 exons spanning 44 kb of DNA, and encodes a 2627 base mRNA transcript. See FIG. 9A & FIG. 9B; Matsubara et al., *Proc Nat'l Acad. Sci. USA,* 1986, Vol. 83, No. 17, pp. 6543-47, incorporated herein by reference. MCAD is an exemplary "control nucleic acid."

While MCAD control nucleic acids are specifically exemplified in the present disclosure, the invention is not limited to the use of this gene as a control nucleic acid. In particular, genes having regions with minimal sequence variability or highly conserved regions and that are present in a subject despite the co-presence of one or more mutations or polymorphisms in certain target genes, a cancerous or precancerous condition, or a foreign pathogenic gene, may provide useful control nucleic acids according to the present methods. In such circumstances it is particularly useful to target regions of one or more of these other control genes that are highly conserved, having minimal or no known sequence variability, for amplification. "Control amplification reagents" are utilized in nucleic acid amplification reactions involving control nucleic acids of the present disclosure to amplify the control nucleic acid or highly conserved region thereof. In this process, under amplification conditions, particular portions of the control nucleic acid are targeted with one or more amplification oligonucleotides and subject to amplification reactions, thereby amplifying (i.e., increasing copy number) the targeted portion of the control nucleic acid.

"Nucleic acid amplification," "amplification reaction," or "amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (e.g., U.S. Pat. No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800,159). LCR amplification uses four or more different oligonucleotides to amplify a target and its complementary strand by using multiple cycles of hybridization, ligation, and denaturation (e.g., U.S. Pat. Nos. 5,427,930 and 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. Nos. 5,422,252; 5,547,861; and 5,648,211).

"Hybridization conditions" refer to the cumulative physical and chemical conditions under which nucleic acid sequences that are completely or partially complementary form a hybridization duplex or complex, usually by standard base pairing. Such conditions are well known to those skilled in the art, are predictable based on sequence composition of the nucleic acids involved in hybridization complex formation, or may be determined empirically by using routine testing (e.g., Sambrook et al., MOLECULAR CLONING, A LABORATORY MANUAL ($2^{nd}$ ed., Cold Spring Harbor Laboratory Press, Cold Spring Harbor, N.Y., 1989) at §§ 1.90-1.91, 7.37-7.57, 9.47-9.51, and 11.47-11.57, particularly §§ 9.50-9.51, 11.12-11.13, 11.45-11.47 and 11.55-11.57 (incorporated herein by reference)).

"Sufficiently complementary" means that a contiguous nucleic acid base sequence is capable of hybridizing to another base sequence by standard base pairing (hydrogen bonding) between a series of complementary bases. Complementary sequences may be completely complementary at each position in an oligomer sequence relative to its target sequence by using standard base pairing (e.g., G:C, A:T or A:U pairing) or sequences may contain one or more positions that are not complementary by base pairing (including abasic residues), but such sequences are sufficiently complementary because the entire oligomer sequence is capable of specifically hybridizing with its target sequence in appropriate hybridization conditions. Contiguous bases in an oligomer are at least 80%, preferably at least 90%, and more preferably completely complementary to the intended target sequence.

"Label" refers to a moiety or compound that is detected or leads to a detectable signal. Any detectable moiety may be a label, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent or chemiluminescent compound), and fluorescent compound.

A "target nucleic acid" as used herein is a nucleic acid comprising a "target sequence" to be amplified. Target nucleic acids may be DNA or RNA as described herein, and may be either single-stranded or double-stranded. The target nucleic acid may include other sequences besides the target sequence, which may not be amplified. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA. "Target amplification reagents" are utilized in nucleic acid amplification reactions involving target nucleic acids of the present disclosure to amplify the target nucleic acid or portion thereof. In this process, under amplification conditions, one or more particular portions of the target nucleic acid is/are targeted with one or more amplification oligonucleotides and subject to amplification reactions, thereby amplifying (i.e., increasing copy number) the targeted portion of the target nucleic acid.

The term "target sequence" as used herein refers to the particular nucleotide sequence of the target nucleic acid that is to be amplified and/or detected. The "target sequence" includes the complexing sequences to which oligonucleotides (e.g., priming oligonucleotides and/or promoter oligonucleotides) complex during the processes of amplification. Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target binding sequence" is used herein to refer to the portion of an oligomer that is configured to hybridize with a target nucleic acid sequence. Preferably, the target binding sequences are configured to specifically hybridize with a target nucleic acid sequence. Target binding sequences may be 100% complementary to the portion of the target sequence to which they are configured to hybridize; but not necessarily. Target-binding sequences may also include inserted, deleted and/or substituted nucleotide residues relative to a target sequence. Less than 100% complementarity of a target binding sequence to a target sequence may arise, for example, when the target nucleic acid is a plurality of strains within a species. It is understood that other reasons exist for configuring a target binding sequence to have less than 100% complementarity to a target nucleic acid.

The term "configured to" denotes an actual arrangement of the polynucleotide sequence configuration of the references oligonucleotide target hybridizing sequence. For example, amplification oligomers that are configured to generate a specified amplicon from a target sequence have polynucleotide sequences that hybridize to the target sequence and can be used in an amplification reaction to generate the amplicon. Also as an example, oligonucleotides that are configured to specifically hybridize to a target sequence have a polynucleotide sequence that specifically hybridizes to the referenced sequence under stringent hybridization conditions.

The phrase "configured to specifically hybridize to" as used herein means that the target hybridizing region of an amplification oligonucleotide, detection probe or other oligonucleotide is designed to have a polynucleotide sequence that could target a sequence of the a target nucleic acid or control nucleic acid, or specific portions thereof. Such an oligonucleotide is not limited to targeting that sequence only, but is rather useful as a composition, in a kit or in a method for the control and target nucleic acids. The oligonucleotide is designed to function as a component of an assay for amplification and detection of the control nucleic acid or target nucleic acid in a sample, and therefore is designed to target a specific control nucleic acid or target nucleic acid in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined.

An "amplification oligomer" or "amplification oligonucleotide" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter-primer" or "promoter provider"). Those skilled in the art will understand that an amplification oligomer that functions as a primer may be modified to include a 5' promoter sequence, and thus function as a promoter-primer. Incorporating a 3' blocked end further modifies the promoter-primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon or other nucleic acid, that the range is inclusive of all whole numbers (e.g. 19-25 contiguous nucleotides in length includes 19, 20, 21, 22, 23, 24 & 25).

The term "amplicon" or the term "amplification product" as used herein refers to the nucleic acid molecule generated during an amplification procedure that is complementary or homologous to a sequence contained within the target sequence. The complementary or homologous sequence of an amplicon is sometimes referred to herein as a "target-specific sequence." Amplicons generated using the amplification oligomers of the current invention may comprise non-target specific sequences. Amplicons can be double stranded or single stranded and can include DNA, RNA or both. For example, DNA-dependent RNA polymerase transcribes single stranded amplicons from double stranded DNA during transcription-mediated amplification procedures. These single stranded amplicons are RNA amplicons and can be either strand of a double stranded complex; depending on how the amplification oligomers are configured. RNA-dependent DNA polymerases synthesize a DNA strand that is complementary to an RNA template. Thus, amplicons can be double stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double stranded DNA. RNA-dependent RNA polymerases synthesize RNA from an RNA template. Thus, amplicons can be double stranded RNA. DNA Dependent RNA polymerases synthesize RNA from double stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination of the current invention. Such representation is not meant to limit the amplicon to the representation shown. Skilled artisans in possession of the instant disclosure will use amplification oligomers and polymerase enzymes to generate any of the numerous types of amplicons; all within the spirit of the current invention.

As used herein "highly conserved" or "highly conserved regions" refers to nucleic acid sequences that vary in less than 1/100 or 1/1000 members of the population.

Tissue Samples

According to the present disclosure nucleic acids can be isolated from any biological sample using conventional methods. Thus, tissue samples of any origin may be utilized according to the present methods. During preservation, tissue samples are often treated with a fixative agent that causes protein cross-linking. Fixatives such as aldehyde fixatives (e.g., formalin/formaldehyde, glutaraldehyde) are typically used; but other fixatives are contemplated within the scope of the disclosure, such as alcohol immersion (see, e.g., Battifora & Kopinski, *J. Histochem. Cytochem.*, 1986, 34:1095, incorporated herein by reference), oxidizing agents (e.g., osmium tetroxide, potassium dichromate, chromic acid, and potassium permanganate), mercurials (e.g., B-5 and Zenker's), picrates, and HOPE fixative (Hepes-glutamic acid buffer-mediated organic solvent protection effect). The main action of aldehyde fixatives is to cross-link amino groups in proteins through the formation of $CH_2$ (methylene) linkage (when using formaldehyde) or a $C_5H_{10}$ cross-link (when using glutaraldehyde). This process, while preserving the structural integrity of the cells and tissue, degrades RNA and DNA present in the tissue.

Tissue samples are also frequently fixed and then embedded in paraffin (i.e., wax). According to the present invention, nucleic acids can be isolated from any wax-embedded biological tissue sample by conventional methods. In one embodiment, the samples are both formalin-fixed and paraffin-embedded.

Microtomy is frequently used to slice FFPE samples into fine sections. DNA is extracted from the sliced sections using, for example, commercially-available FFPE DNA extraction kits (e.g., QIAMP FFPE DNA Extraction Kit, Qiagen GmbH, Hilden, Germany). DNA from these samples is typically degraded due to the action of the formalin fixative. Moreover, the amount of DNA in the sliced sample often varies greatly and any particular section of tissue often contains a mixture of DNA types, for example a mixture of mutant DNA and wildtype DNA. The present methods and compositions are sensitive enough to permit the detection of at least about 1% mutant DNA in an otherwise wild-type sample.

In an exemplary extraction procedure paraffin is dissolved in xylene and removed. The sample is then lysed under denaturing conditions with a short proteinase K digestion and incubated at 90° C. to reverse formalin cross-linking. DNA binds to the membrane and contaminants flow through or are washed away. Purified and concentrated DNA is then eluted in buffer or water from the membrane.

In a frequent embodiment the purified and concentrated DNA comprises Medium Chain Acyl-CoA Dehydrogenase (MCAD) gene DNA in addition to one or more target nucleic acid molecules.

Exemplary Assays

FIG. 1A describes the results of an exemplary post-amplification gel electrophoresis assay of an amplified and purified target oligonucleotide in addition to three different MCAD oligonucleotides of 100 bases, 150 bases, and 200 bases. In this example, the MCAD amplicons were prepared utilizing three different unlabeled reverse primers and a single labeled forward primer. This figure depicts equal signal intensities of each of the MCAD controls, here at about 3000 RFUs. The target peak (e.g., from a KRAS mutant) can be visualized having a lower intensity and lying between the 100 base and 150 base peaks of the MCAD controls.

Although control amplicons of 100, 150, and 200 bases are specifically exemplified, the particular sizes of the control amplicons are not limited. In particular, any particular selection of amplicon sizes may be chosen provided that at least two different control amplicons are derived from the same gene. Preferably at least three control amplicons are derived from the same gene, provided they have different sizes that are discernable from one another by, for example, gel electrophoresis. In frequent embodiments, the sizes of the control amplicons are chosen with reference to the one or more target genes that are to be assayed to ensure that the target gene amplicon(s) are not co-extensive in size/length with one or more of the control peaks. When mutations or polymorphisms are targeted by the assay, often the sizes of the control amplicons are chosen depending on the number and sizes of target amplicons, each containing one or more polymorphisms, which could be present in any particular assay. For example, a particular sample may harbor one or more polymorphisms targeted by a multi-marker assay and, in order to minimize the number of target primers utilized, or to design the most appropriate primers, choices must be made about various target amplicon sizes. Often in such circumstances it is advantageous to choose the control amplicon sizes/lengths in a manner that does not interfere with target primer design choices. Thus, control amplicon sizes/lengths can vary within any size range that is practical to the assay being performed.

In frequently preferred embodiments the control reagents, such as MCAD controls, are provided in a multiplex format such that multiple different-sized amplicons are produced and detected from the same target control gene to provide a control ladder.

Figure 1C:
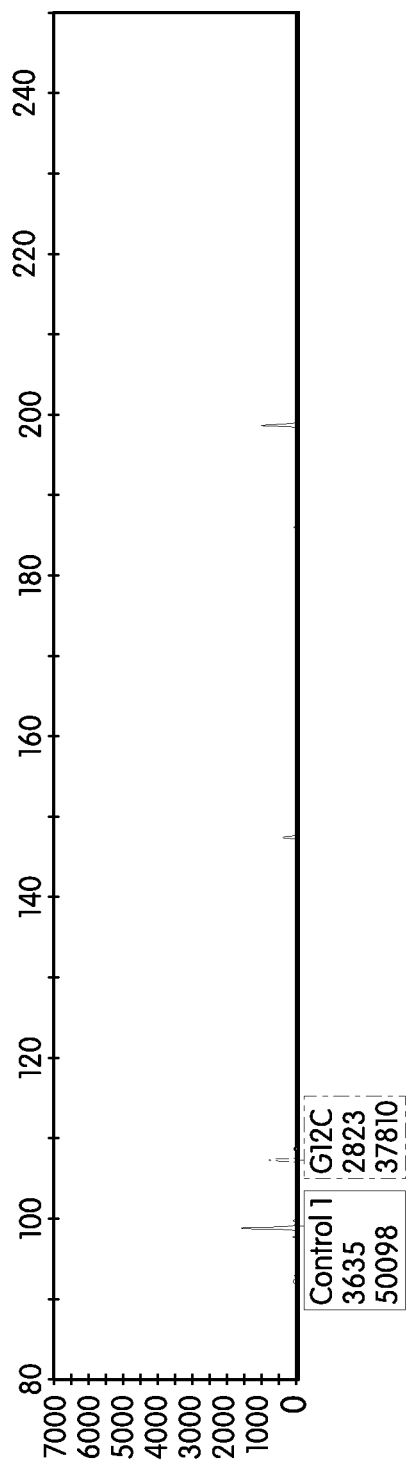
Figure 2A:
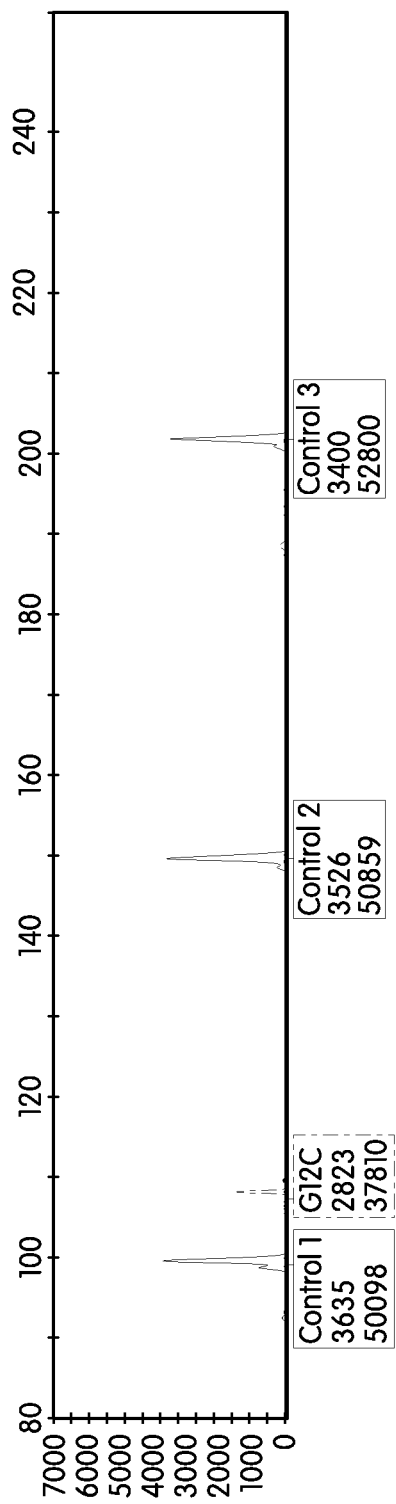
FIG. 2A, FIG. 2B, FIG. 2C depict exemplary results of an assay of sufficient DNA (FIG. 2A), reduced DNA (FIG. 2B), and very little DNA (FIG. 2C) in a sample using control reagents of the present disclosure. The X-coordinate depicts amplicon size, and the Y-coordinate depicts fluorescence intensity in RFUs.
Figure 2B:
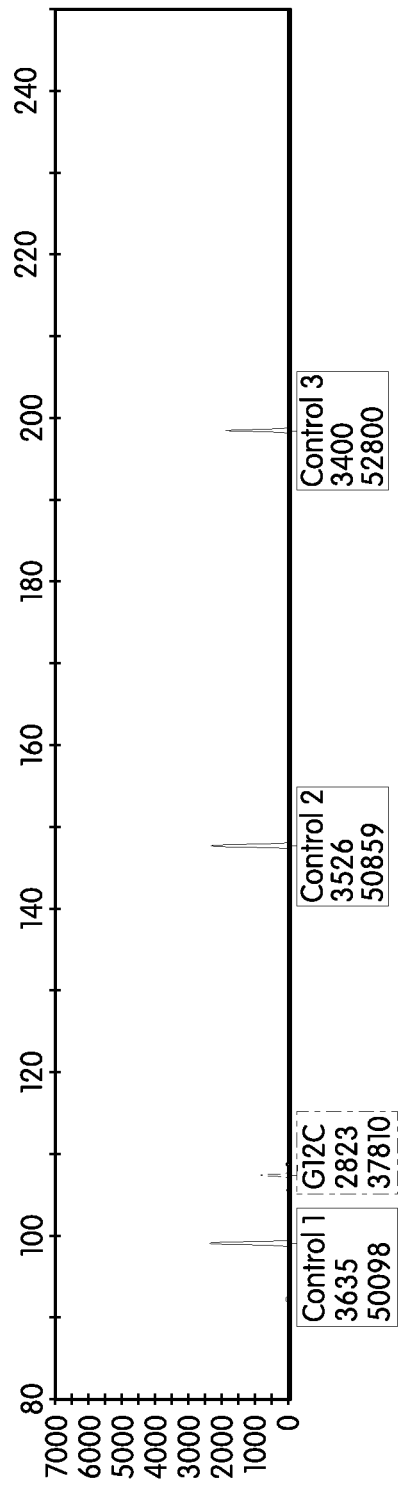
Figure 2:
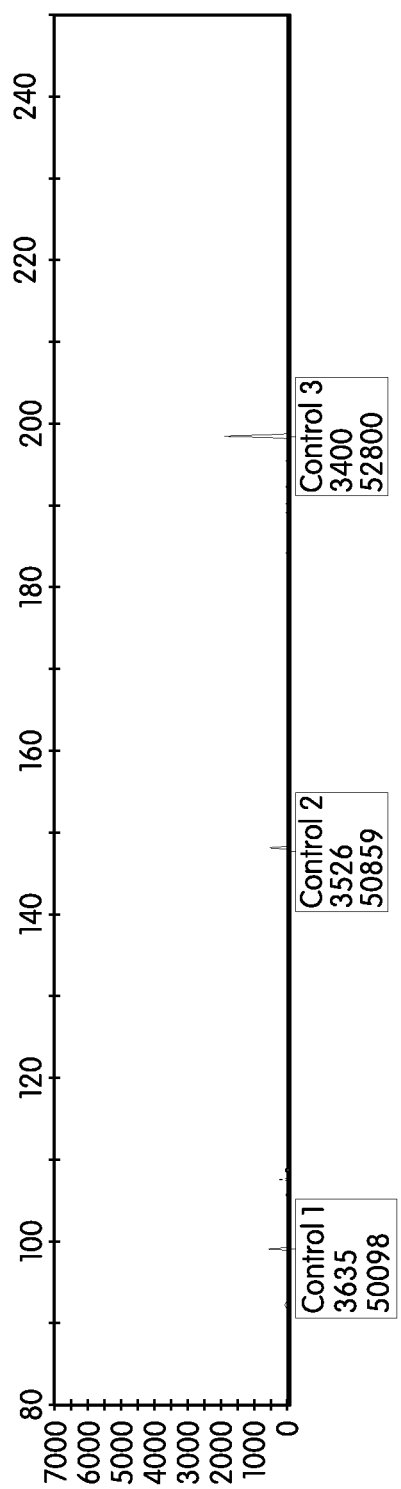

The control peaks provide a reference against which the analytical peaks can be compared allowing the proportion of the amplicon of interest to be measured (see, e.g., FIGS. 1A, 1B, 1C, 2A, 2B, 2C, 3A, 3B, 3C, 5A, 5B, 5C, 8). This is important when dealing with mixed cell populations. In addition, the control peaks provide a measure of the amplifiability and concentration of the sample DNA (see FIGS. 1A, 1B, 1C, 2A, 2B, 2C, 3A, 3B, 3C). For example, the controls of the present invention, since they are internal controls originating from the same sample being assayed for a particular target gene, signal the degradation state of the overall sample. These aspects are important when dealing with inhibited and/or degraded samples to achieve maximum sensitivity of the assay. In this regard, FIG. 1A depicts a post-amplification, gel electrophoresis assay of good quality DNA. FIG. 1B depicts a post-amplification, gel electrophoresis assay of acceptable quality DNA. And, FIG. 1C depicts a post-amplification, gel electrophoresis assay of very degraded DNA, showing the loss of the third control peak (200 bases) and near-loss of the second control peak (150 bases). FIG. 2A, FIG. 2B, FIG. 2C, in turn, depict the results of post-amplification, gel electrophoresis assays of a sample having sufficient DNA levels for maximum assay sensitivity (FIG. 2A), a sample having a reduced DNA levels that may limit assay sensitivity (FIG. 2B), and a sample having very little DNA that will reduce assay sensitivity.

Overall, using a multiplexed internal PCR control provides an indication of the degree of degradation of the sample DNA. The control is typically used in an amplification assay, which typically presents a number of analysis challenges. For example, the target sequence may not be present in every cell of a given tissue sample. In the case of an FFPE tissue sample, as indicated above, the sample has been treated in a manner that results in heavily degraded DNA in the sample. Similarly, preserved tissue samples may contain chemicals that act as PCR inhibitors, such as heparin, which typically interfere with PCR assays and results.

The internal controls of the present disclosure were designed to account for each of the above factors and to provide a variety of benefits. For example, by establishing a specification for the performance of the control reaction, it has been possible to establish a lower level of sensitivity for the target reaction.

Since the internal controls act as a reference value for the target reaction, a measure of quantity and quality is also provided. In certain embodiments, the internal control peaks represent 100% of the nucleic acids in the sample being tested. In other words, the control peaks are representative of the amplifiable amount of wild-type and mutant nucleic acids in the sample. In other embodiments, the internal control peaks attributable to the internal control, e.g., MCAD-type controls, represent between about 50% to about 100% of nucleic acids in the sample being tested. The sensitivity of detection of a target nucleic acid molecule (e.g., a tumor-derived nucleic acid molecule) within a background of non-target nucleic acid molecules can be determined by comparing the target nucleic acid molecule signal (i.e., peak height) to internal control peak heights. When fluorescent labeling schemes are utilized the peak heights are often represented by particular RFU readings.

In a particular set of embodiments the balance of the assay is adjusted so that the internal control peak heights are equal to target sequence peak heights in the presence of 20% of target sequence in the sample. For example, FIG. 4A, FIG. 4B, FIG. 4C, FIG. 4D depict certain examples of balancing the control peak levels with 100% wild-type nucleic acids in a sample. Thus, in this example, if an unknown sample is tested and the target signal is equivalent to the internal control peak the amount of target sequence present in the sample is determined to be 20%. Similarly, if the target peak is $1/20^{th}$ of the signal of the control peak the amount of target sequence is determined to be 1%. Overall, the control peak signal is independent of the target nucleic acid signal and is most frequently designed to provide a peak intensity level that is indicative of the total amount of amplifiable nucleic acids in the sample, regardless of the amount of target nucleic acid in the sample. Comparison of target signal to internal control signal can therefore provide useful information regarding the sensitivity of detection of the assay. To achieve a sensitivity of 1% the measurable peak is generally discernable above background. Though background signals may vary, one exemplary level of background signal is about 100 RFUs and the internal control signal is at least about 2000 RFUs. The internal control assay, therefore, can operate to validate the sensitivity limit with each individual sample; for example, as depicted in FIG. 2A, FIG. 2B, FIG. 2C, FIG. 3A, FIG. 3B, FIG. 3C, FIG. 5A, FIG. 5B, FIG. 5C.

Figure 3A:
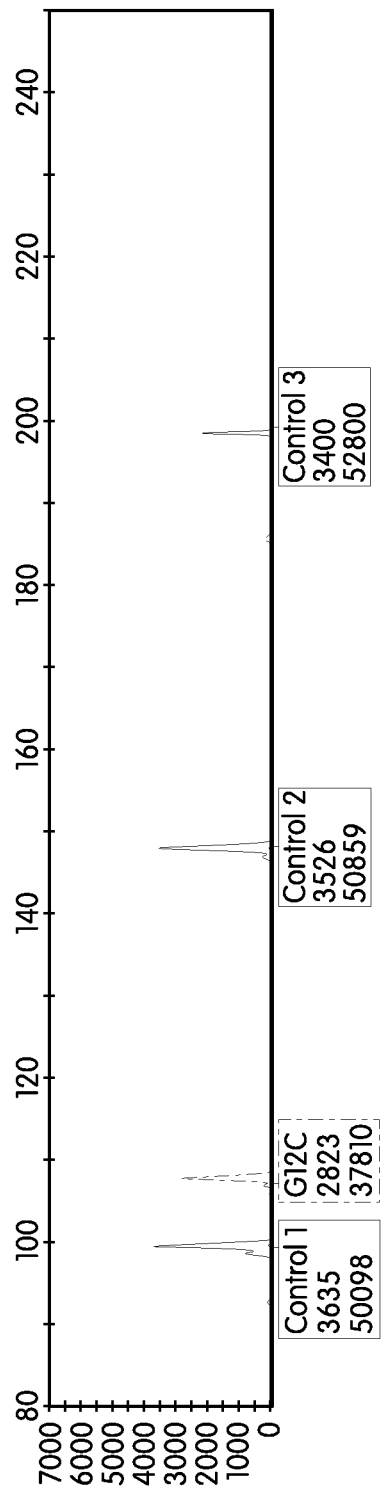
FIG. 3A, FIG. 3B, FIG. 3C depict exemplary results of an assay for mutant DNA and control DNA. The X-coordinate depicts amplicon size, and the Y-coordinate depicts fluorescence intensity in RFUs.
Figure 3B:
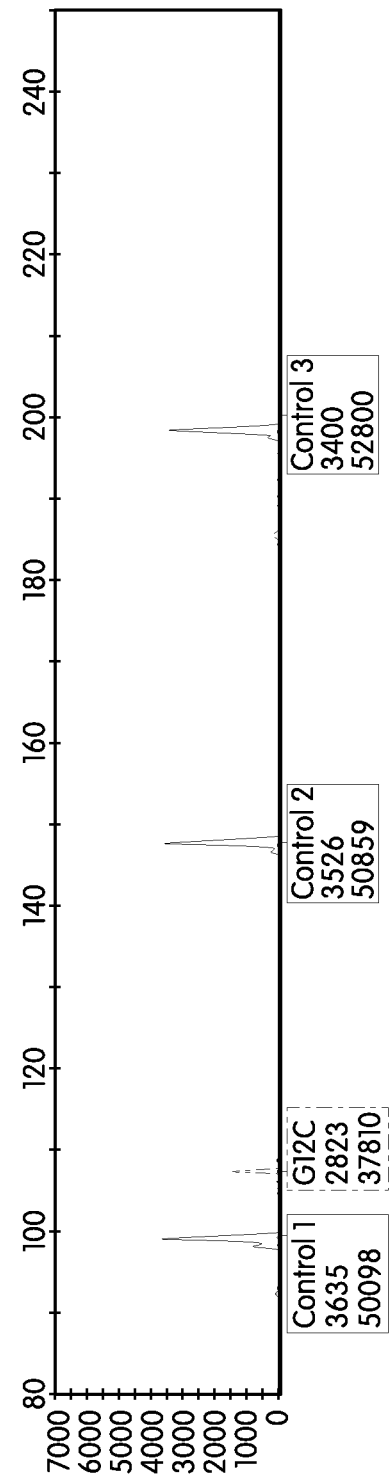
Figure 3:
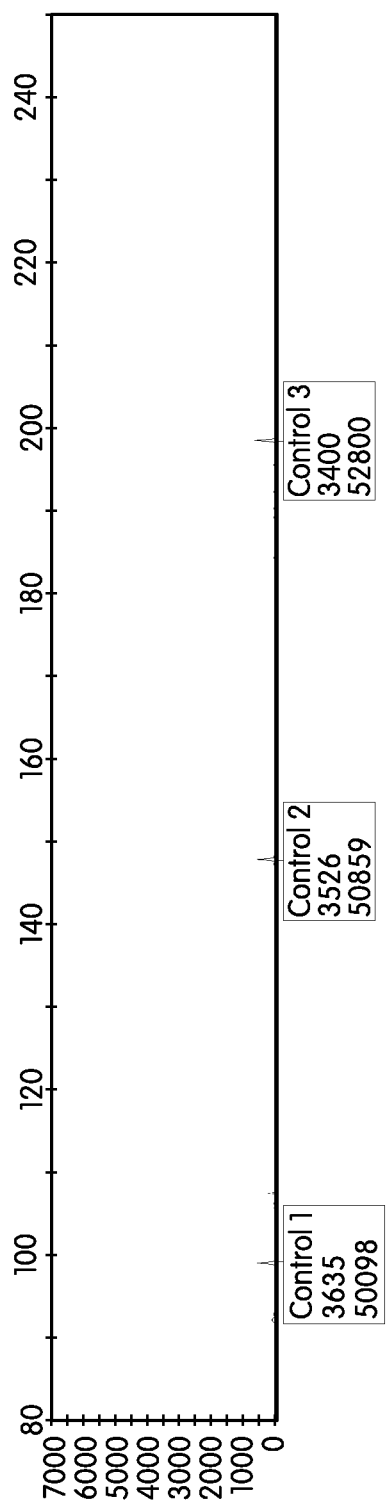
Figure 4A:
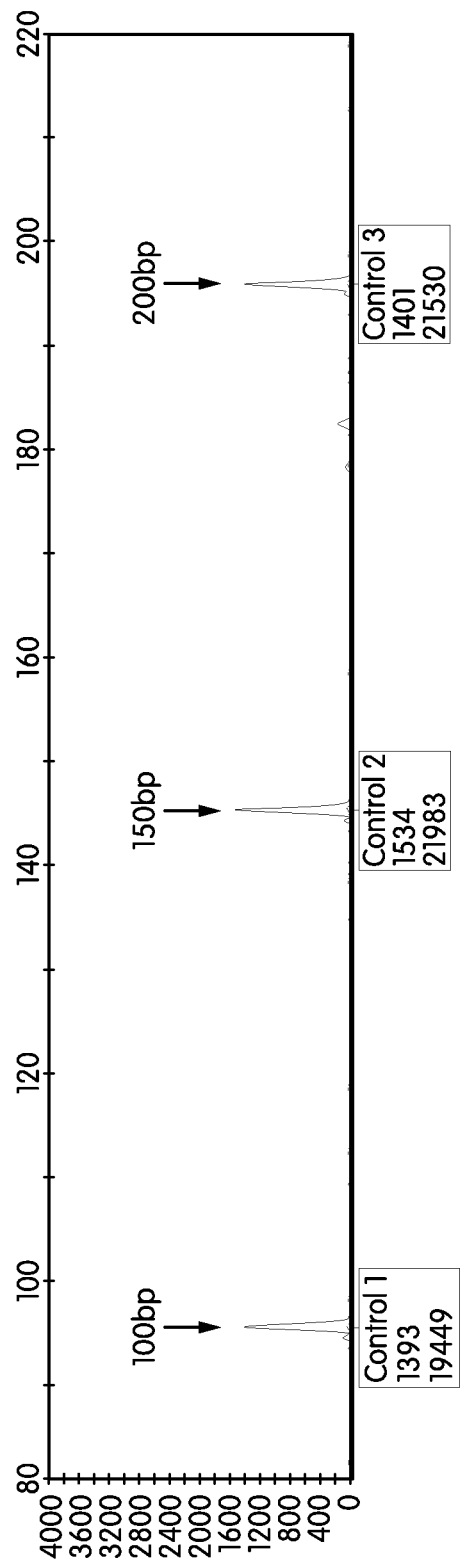
FIG. 4A, FIG. 4B, FIG. 4C, FIG. 4D depict results of an assay of control balancing with 100% wildtype DNA. The X-coordinate depicts amplicon size, and the Y-coordinate depicts fluorescence intensity in RFUs.
Figure 4B:
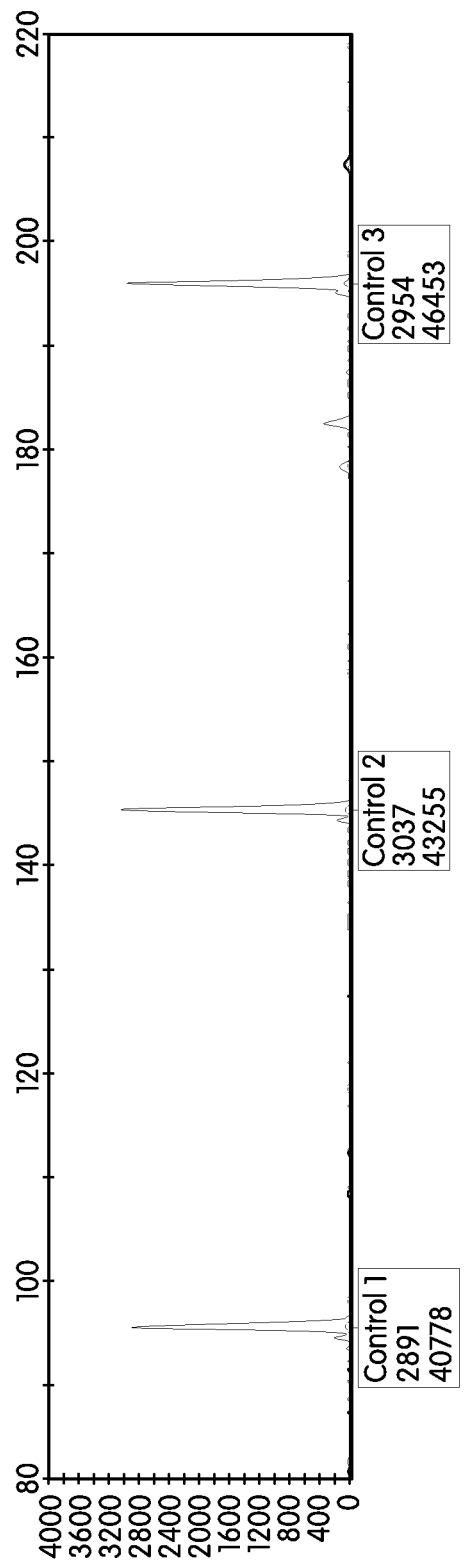
Figure 4C:
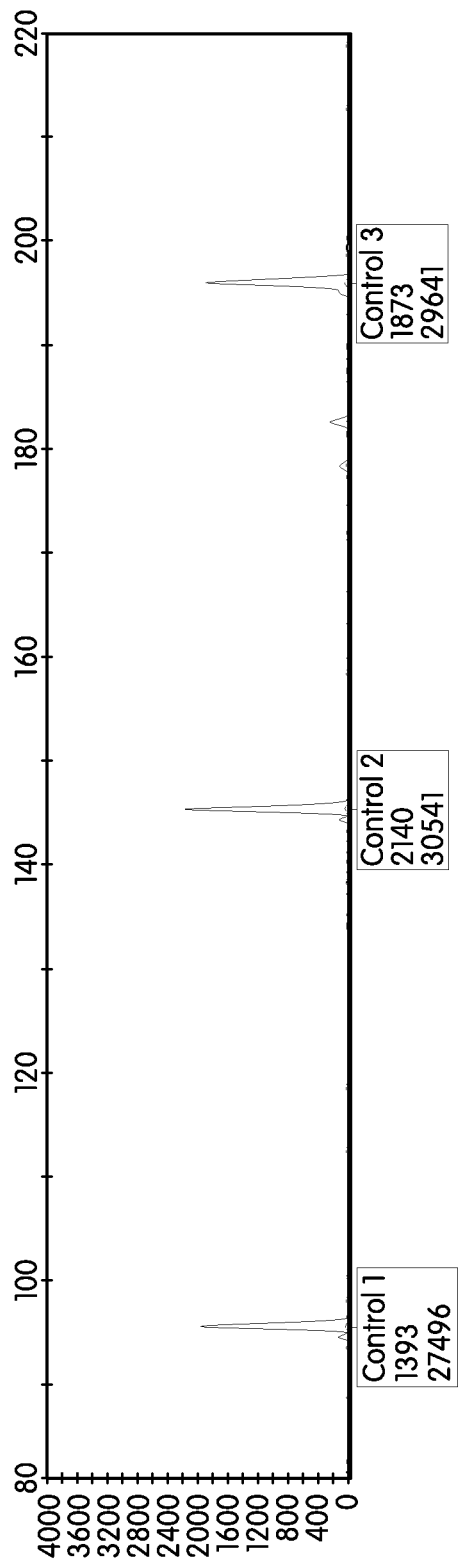
Figure 4D:
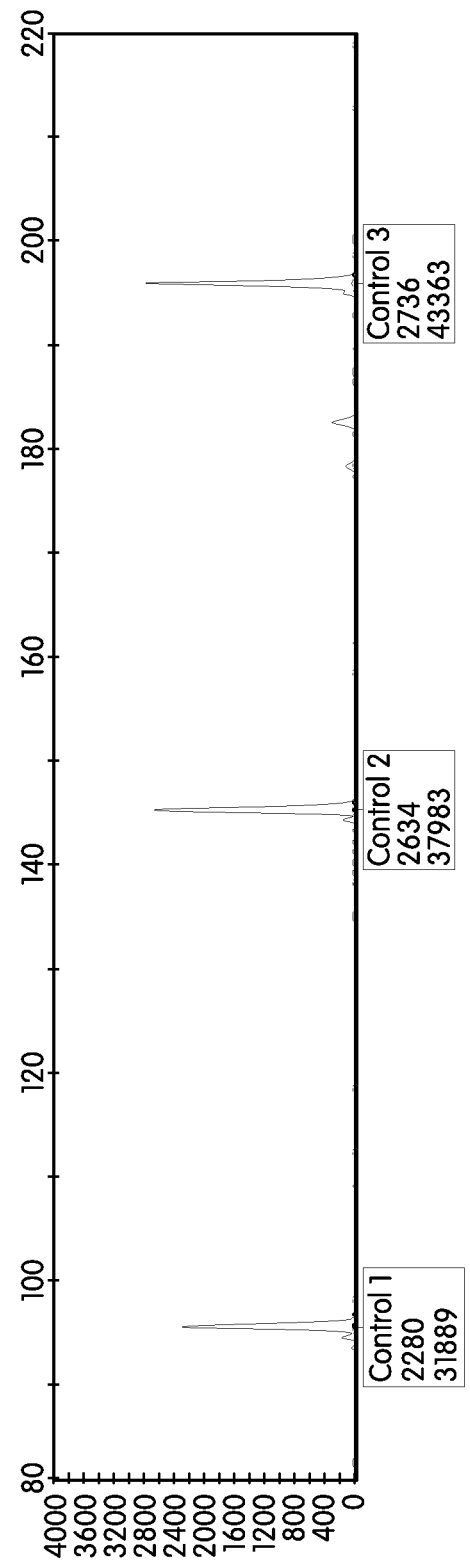

FIG. 3A depicts the formulation of the control peak to have approximately equal intensity with a mutant sequence peak, when the mutant is present at 20%. In other words, when the target is present in the sample at 20% of the total tested DNA, its peak height is approximately equal to the peak height of the control. FIG. 3B shows the detection of a 1% mutant sequence peak, which is $1/20^{th}$ of the control peak. FIG. 3C shows a sample with a low concentration of amplifiable nucleic acids (determined by virtue of the low control peaks). The situation depicted in FIG. 3C, with the low level of amplifiable nucleic acids, would present complications in identifying a 1% level of mutant DNA in the sample. With regard to FIG. 5A, FIG. 5B, FIG. 5C, these show exemplary control peaks in combination with target nucleic acid (i.e., mutant KRAS) peaks. The mutant peaks are circled and represent about, or up to, 20% of the total DNA tested.

Moreover, with the presently described methods and compositions, it is also possible to estimate the amplifiability of the sample nucleic acids by comparing the signal strength of the control to the nominal amount of nucleic acids present in the sample (see, e.g., FIG. 1A, FIG. 1B, FIG. 1C, FIG. 2A, FIG. 2B, FIG. 2C, FIG. 3A, FIG. 3B, FIG. 3C). In this regard, PCR amplification is often inhibited by certain chemicals, proteins, and/or contaminants that are co-purified during the nucleic acid extraction process. Such contaminating materials act on the polymerase enzyme responsible for nucleic acid amplification. Both target and internal control amplification are equally affected by this inhibition process resulting in an equal reduction in the measurable amplified signals of internal control and target sequences. As such, use of the present internal controls eliminates the need to quantify the amplifiability of sample nucleic acids.

The presently described methods and compositions also allow a qualitative indication of the degree that nucleic acids within a sample have degraded (see, e.g., FIG. 1A, FIG. 1B, FIG. 1C, FIG. 6, FIG. 7). For example, in certain embodiments three amplicons of differing size (for example 100, 150 and 200 bases) are amplified using reagents specific for the particular sized nucleic acid molecule. The efficiency at which each sized amplicon is amplified is dependent upon the amount of nucleic acid molecule fragments of appropriate size available for amplification. DNA extracted from FFPE samples is generally subject to significant degradation, which results in the extracted DNA fragments being reduced in size. In general, the more highly degraded the sample is, the smaller the fragment sizes. A comparison of the internal control peaks, each corresponding to a different sized control amplicon, with one-another will indicate the degree of degradation of the sample being tested. For example, a degraded sample may not contain a large concentration of long nucleic acid fragments (e.g., in the 150 or 200 base size range), thus decreasing or eliminating the larger control peaks (e.g., FIGS. 1B, 1C, 7). In contrast, a nucleic acid molecule sample that is not significantly degraded will generally exhibit three signals of equal size (e.g., FIG. 1A, FIG. 2A, FIG. 2B, FIG. 2C, FIG. 3A, FIG. 3B, FIG. 3C, FIG. 4A, FIG. 4B, FIG. 4C, FIG. 4D, FIG. 5A, FIG. 5B, FIG. 5C, FIG. 6).

FIG. 8 depicts the results of an assay of a mixed sample containing multiple mutant BRAF and KRAS nucleic acids in addition to internal controls (MCAD). The control peaks are located in the boxes, the BRAF mutant peak (V600E) is located in the oval, and the multiple KRAS peaks (G12R, G12C, G12S, G12A, G12V, G12D, and G13D) are unmarked. In such an assay the individual peaks of each nucleic acid are clearly discernable above background and from one another. The peak levels also provide a qualitative measure of the amount of mutant nucleic acid in the sample, as described above, with reference to the control peak levels. Exemplary MCAD primers are set forth in Table 1.

scriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202, and 4,800,159; Mullis et al., *Meth. Enzymol.*, 1987, 155: 335; and, Murakawa et al., *DNA*, 1988, 7: 287 (each of which is incorporated herein by reference).

Transcription-Mediated Amplification (U.S. Pat. Nos. 5,480,784 and 5,399,491, each of which is incorporated herein by reference), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518 (each of which is incorporated herein by reference). In a variation described in U.S. Pat. No. 7,374,885 (incorporated herein by reference), TMA optionally incorporates the use of blocking moieties, terminating moieties, and other modifying moieties to aid in the reduction of side-product formation.

TABLE 1

| Primer | Nucleotide Sequence | SEQ ID NO: |
|---|---|---|
| MCAD F (NED) | NED-GTACTTCACAAATTCAAAGACTTATTGTATCC | 1 |
| MCAD F2 (NED) | NED-GTACTTCACAAATTCAAAGACTTATTGTAGCC | 2 |
| MCAD 80R | TCAATATTTCTACAGTAATTTTTTAATTTTTG | 3 |
| MCAD R2 80 | TCAATATTTCTACAGTAATTTTTTAATTTTTGTACTTG | 4 |
| MCAD R (100) | CTTGTGTTCTAGTTATTCAATATTTCTACAGTAATTTT | 5 |
| MCAD R (150) | CTGGAAAAAACGTTAAAGCCCTTTCT | 6 |
| MCAD R (200) | CTACTATAATAGGCAGTTGCTTAGATTTAATATAAGAGG | 7 |
| MCAD R (300) | TCTAGGTTAATGTAATTCAAGTAAAGTGGTACTAAAGAAAAC | 8 |

Amplification and Detection Methods

Genomic DNA (gDNA), complementary DNA (cDNA), and messenger RNA (mRNA) may be amplified prior to or simultaneous with detection. Illustrative non-limiting examples of nucleic acid amplification techniques include, but are not limited to, polymerase chain reaction (PCR), reverse transcription polymerase chain reaction (RT-PCR), Transcription-Mediated Amplification (TMA), ligase chain reaction (LCR), strand displacement amplification (SDA), and nucleic acid sequence-based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188 (each of which is incorporated herein by reference)), commonly referred to as PCR, uses multiple cycles of denaturation, annealing of primer pairs to opposite strands, and primer extension to exponentially increase copy numbers of a target nucleic acid sequence. In a variation called RT-PCR, reverse tran- The ligase chain reaction (Weiss, R., *Science*, 1991, 254: 1292, incorporated herein by reference), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA*, 1992, 89: 392-396; U.S. Pat. Nos. 5,270,184 and 5,455,166 (each of which is incorporated herein by reference)), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Patent No. 0684315, incorporated herein by reference).

Other amplification methods include, for example: nucleic acid sequence-based amplification (U.S. Pat. No. 5,130,238), commonly referred to as NASBA; a method that uses an RNA replicase to amplify the probe molecule itself (Lizardi et al., *BioTechnol.*, 1988, 6: 1197), commonly referred to as Qβ replicase; a transcription-based amplification method (Kwoh et al., *Proc. Natl. Acad. Sci. USA*, 1989, 86:1173); and a self-sustained sequence replication (Guatelli et al., *Proc. Natl. Acad. Sci. USA*, 1990, 87: 1874) (each of which is incorporated herein by reference). For further discussion of certain known amplification methods see Persing, David H., "In Vitro Nucleic Acid Amplification Techniques" in DIAGNOSTIC MEDICAL MICROBIOLOGY: PRINCIPLES AND APPLICATIONS pp. 51-87 (Persing et al., Eds., American Society for Microbiology, Washington, D.C. (1993)) (incorporated herein by reference).

Non-amplified or amplified nucleic acids can be detected by any conventional means. For example, the target nucleic acids and MCAD controls can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174; Nelson et al., Nonisotopic Probing, Blotting, and Sequencing, ch. 17 (Larry J. Kricka ed., 2d ed. 1995) (each of which is incorporated herein by reference).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205 (each of which is incorporated herein by reference). Another method for determining the quantity of target sequence initially present in a sample, but which is not based on a real-time amplification, is disclosed in U.S. Pat. No. 5,710,029 (incorporated herein by reference).

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs, including fluorescence resonance energy transfer (FRET) labels, are disclosed in, for example U.S. Pat. Nos. 6,534,274 and 5,776,782 (incorporated herein by reference).

The interaction between two molecules can also be detected, e.g., using fluorescence energy transfer (FRET) (see, e.g., U.S. Pat. Nos. 5,631,169 & 4,968,103, each of which is incorporated herein by reference). A fluorophore label is selected such that a first donor molecule's emitted fluorescent energy will be absorbed by a fluorescent label on a second, "acceptor" molecule, which in turn is able to fluoresce due to the absorbed energy.

Alternately, the "donor" protein molecule may simply utilize the natural fluorescent energy of tryptophan residues. Labels are chosen that emit different wavelengths of light, such that the "acceptor" molecule label may be differentiated from that of the "donor." Since the efficiency of energy transfer between the labels is related to the distance separating the molecules, the spatial relationship between the molecules can be assessed. In a situation in which binding occurs between the molecules, the fluorescent emission of the "acceptor" molecule label should be maximal. A FRET binding event can be conveniently measured through standard fluorometric detection means well known in the art (e.g., using a fluorometer).

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed, for example, in U.S. Pat. Nos. 5,925,517 and 6,150,097 (each of which is incorporated herein by reference).

Other self-hybridizing probes are well known to those of ordinary skill in the art. By way of non-limiting example, probe binding pairs having interacting labels, such as those disclosed in U.S. Pat. No. 5,928,862 (incorporated herein by reference) can be adapted for use in the methods of the present invention. Probe systems used to detect single nucleotide polymorphisms (SNPs) can also be utilized in the present invention. Additional detection systems include "molecular switches," as disclosed, for example, in U.S. Publ. No. 20050042638 (incorporated herein by reference).

Other probes, such as those comprising intercalating dyes and/or fluorochromes, are also useful for detection of amplification products methods of embodiments of the present disclosure. See, e.g., U.S. Pat. No. 5,814,447 (incorporated herein by reference).

Any of these compositions, alone or in combination with other compositions of the present disclosure, may be provided in the form of a kit.

While the present invention has been described and shown in considerable detail with reference to certain illustrative embodiments, including various combinations and sub-combinations of features, those skilled in the art will readily appreciate other embodiments and variations and modifications thereof as encompassed within the scope of the present invention. Moreover, the descriptions of such embodiments, combinations, and sub-combinations is not intended to convey that the inventions requires features or combinations of features other than those expressly recited in the claims. Accordingly, the present invention is deemed to include all modifications and variations encompassed within the spirit and scope of the following appended claims.

EXAMPLE

A multiplex assay was prepared to determine whether a patient has a KRAS or BRAF mutation using DNA extracted from an FFPE tissue. The exemplary assay tests for 6 mutations located on codon 12 and 1 mutation on codon 13 of KRAS, and mutations on codon 600 of BRAF. The target mutations differ by 1 base pair (missense mutation) causing one amino acid to be replaced with another, for example, KRAS G12R, KRAS G12S, KRAS G12C, KRAS G12D, KRAS G12A, KRAS G12V, KRAS G13D, and BRAF V600E.

Microtomy was used to slice the sample into fine sections. DNA was extracted using the QIAMP FFPE DNA Extraction Kit (Qiagen GmbH, Hilden, Germany). The sample was contacted with the KRAS/BRAF PCR Mix which also contained an MCAD control amplification reagent mix as an internal control. 2.5 uL of DNA was amplified using ARMS PCR (12.5 uL Total Volume), purified in a PERFORMA® spin column and then 3 uL of purified amplicon was run on a genetic analyzer (3130XL Genetic Analyzer, Life Technologies Corp., Carlsbad, Calif.) using 15 uL ABI Hi-Di and a LIZ600 Size Standard (18 uL Total Volume).

MCAD Primers amplified DNA to create 3 peaks at 100, 150 and 200 bases (FIG. 8). KRAS and BRAF Mutant Peaks are located between the MCAD 100 and 150 base peaks (FIG. 8).

Figure 5A:
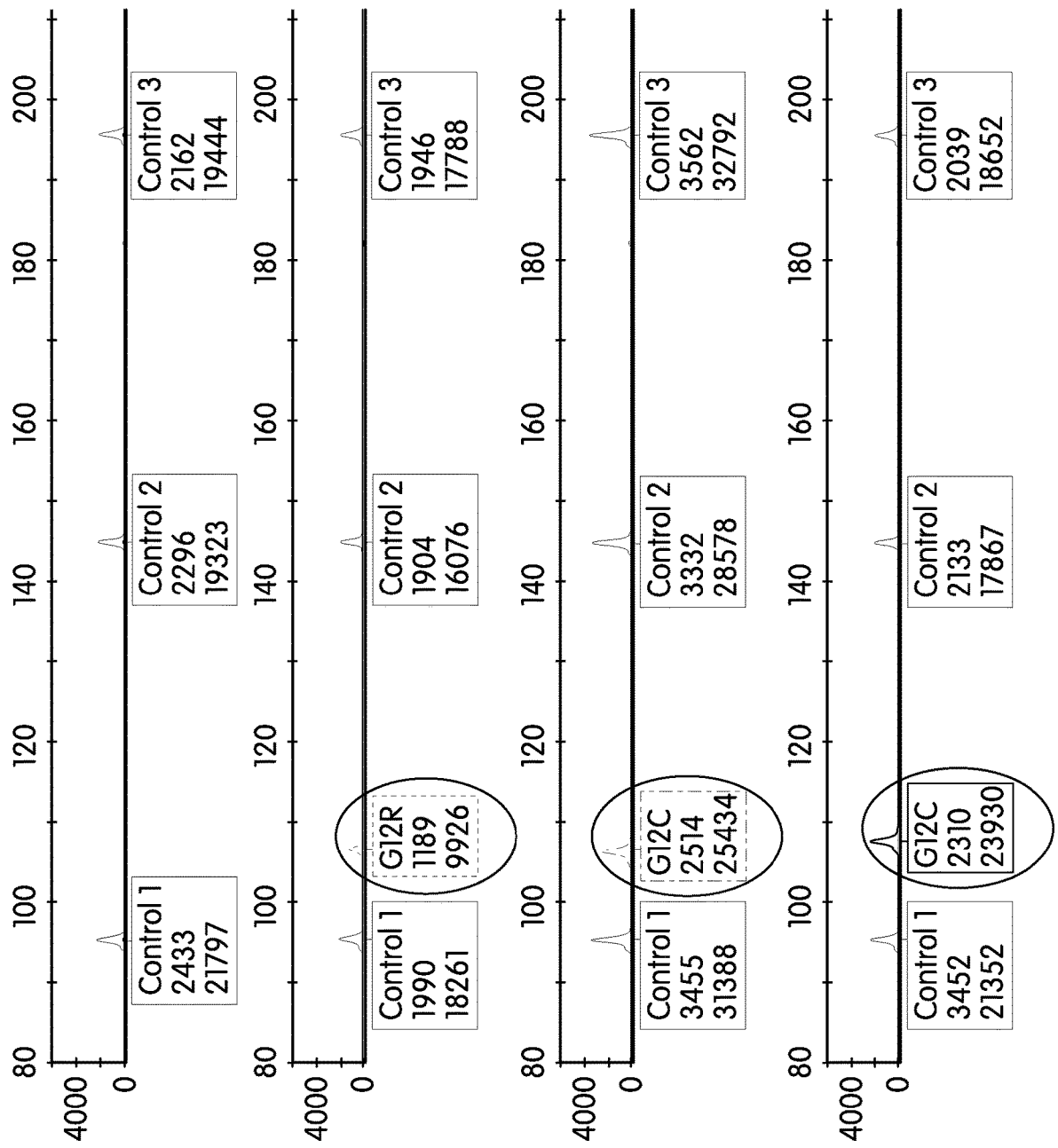
FIG. 5A, FIG. 5B, FIG. 5C depict results of an assay of control balancing with 20% mutant DNA in wildtype DNA.
Figure 5:
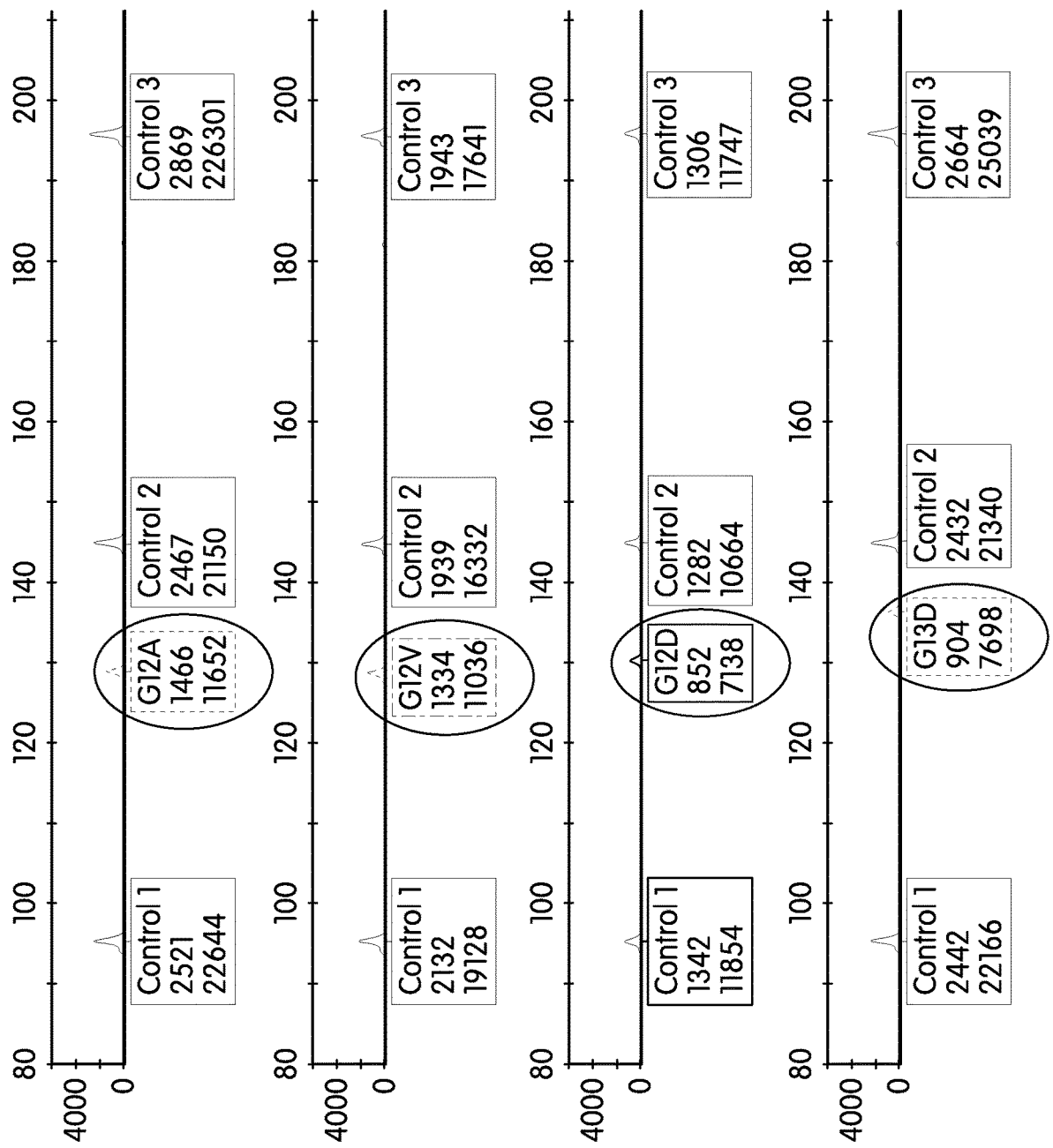
Figure 5C:
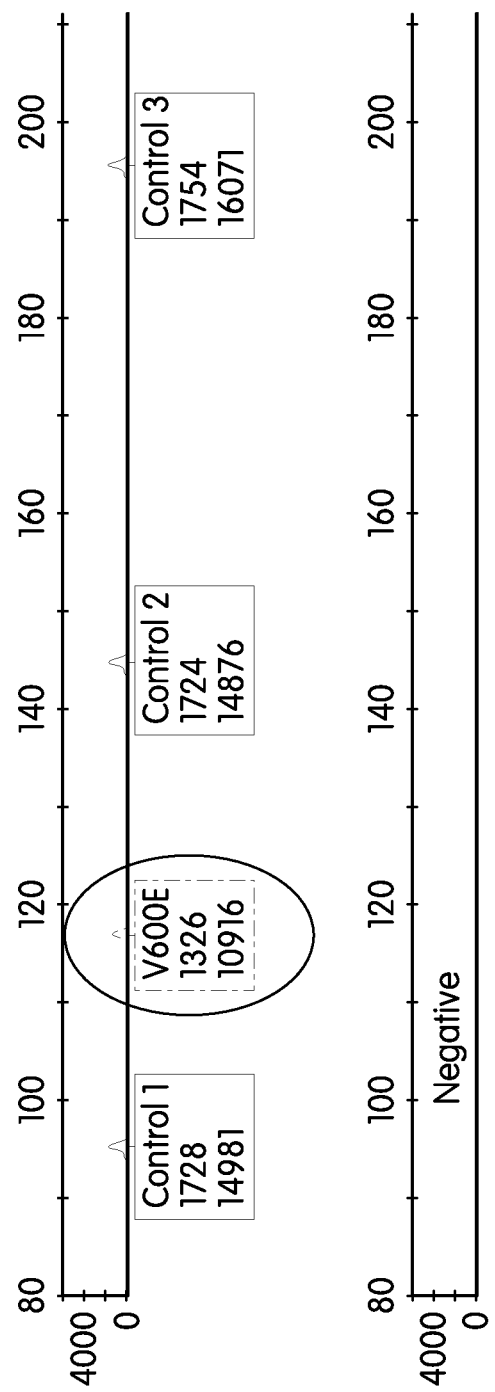

The assay was balanced using gDNA from cell lines containing mutant heterozygous or homozygous DNA mixed with wildtype gDNA (FIG. 4A, FIG. 4B, FIG. 4C, FIG. 4D, FIG. 5A, FIG. 5B, FIG. 5C). 20% mixture of mutant to wild-type gDNA was used to balance with the MCAD peaks (FIG. 5A, FIG. 5B, FIG. 5C).

What is claimed is:

1. A method of conducting an amplification assay for detection of a target nucleic acid, the method comprising:

(a) contacting a biological sample with a control amplification reagent and a target amplification reagent to form a reaction mixture, wherein the control amplification reagent comprises two or more pairs of amplification oligonucleotides capable of amplifying a medium chain acyl-coenzyme A dehydrogenase (MCAD) nucleic acid molecule or a complement thereof, and wherein the target amplification reagent comprises a pair of amplification oligonucleotides capable of amplifying a non-MCAD target nucleic acid of interest or a complement thereof, wherein said non-MCAD target nucleic acid is a chromosomal DNA;
(b) subjecting the reaction mixture to amplification conditions to produce an amplification mixture, whereby
(i) two or more regions of the MCAD nucleic acid molecule, if present in the biological sample, are amplified to produce two or more detectably distinguishable MCAD amplicons, each having a different length, wherein the two or more different length MCAD amplicons form a size control ladder comprised of amplicons of increasing length, and
(ii) a region of the target nucleic acid, if present in the biological sample, is amplified to produce at least one detectable target amplicon;
(c) evaluating the amplification mixture to detect the two or more MCAD amplicons and the target amplicon; and
(d) comparing the detected MCAD amplicons with the detected target amplicon to evaluate the amount and quality of the target nucleic acid and/or the MCAD nucleic acid molecule present in the biological sample.

2. The method of claim 1, wherein step (d) comprises evaluating the amplification mixture to detect to the length and amount of each MCAD amplicon, wherein the biological sample is determined to contain degraded nucleic acid molecules that may adversely impact molecular analysis of the biological sample if:
(1) the amount detected of each of the two or more MCAD amplicons is smaller than the amount detected of each of the two or more MCAD amplicons in a comparative control sample;
(2) the amount detected of each of the two or more MCAD amplicons in the size control ladder decreases as the length of each MCAD amplicon in the size control ladder increases; or
(3) one or more of the MCAD amplicons are undetectable after production of the amplification mixture.

3. The method of claim 1, wherein the control amplification reagent comprises three or more pairs of amplification oligonucleotides capable of amplifying the MCAD nucleic acid molecule or a complement thereof.

4. The method of claim 1, wherein each of the two or more pairs of control amplification reagent amplification oligonucleotides comprises a sense amplification oligonucleotide and an antisense amplification oligonucleotide, and wherein the sense amplification oligonucleotide of each of the two or more pairs of control amplification reagent amplification oligonucleotides comprises the same oligonucleotide sequence.

5. The method of claim 1, wherein each of the two or more pairs of control amplification reagent amplification oligonucleotides comprises a sense amplification oligonucleotide and an antisense amplification oligonucleotide, and wherein the antisense amplification oligonucleotide of each of the two or more pairs of control amplification reagent amplification oligonucleotides comprises the same oligonucleotide sequence.

6. The method of claim 1, wherein one or more of the amplification oligonucleotides is/are labeled.

7. The method of claim 1, wherein the biological sample is a preserved biological sample.

8. The method of claim 1, wherein the biological sample comprises a tissue sample.

9. The method of claim 8, wherein the tissue sample comprises a formalin-fixed paraffin-embedded (FFPE) tissue sample.

10. The method of claim 1, wherein the amplification conditions comprises a nucleic acid amplification technique selected from the group consisting of polymerase chain reaction (PCR), reverse transcription polymerase chain reaction (RT-PCR), transcription-mediated amplification (TMA), ligase chain reaction (LCR), strand displacement amplification (SDA), and nucleic acid sequence-based amplification (NASBA).

11. The method of claim 10, wherein the nucleic acid amplification technique is polymerase chain reaction (PCR).

12. The method of claim 10, wherein the nucleic acid amplification technique is transcription-mediated amplification (TMA).

13. The method of claim 1, wherein the two or more MCAD amplicons and the target amplicon are detected by hybridization of each of said amplicons to a detectably labeled probe and measurement of the resulting hybrids.

14. The method of claim 13, wherein the detectable label is a fluorescent or chemiluminescent compound.

15. The method of claim 1, wherein evaluating the amplification mixture comprises a real-time evaluation of an amplification process.

16. The method of claim 15, wherein each of the two or more MCAD amplicons and the target amplicon is detected in real-time using a self-hybridizing probe.

17. The method of claim 16, wherein the self-hybridizing probe is selected from the group consisting of a molecular torch, a molecular beacon, and a molecular switch.

18. The method of claim 16, wherein the self-hybridizing probe comprises a pair of interacting labels.

19. The method of claim 18, wherein the pair of interacting labels is selected from the group consisting of
(a) a pair of fluorescence resonance energy transfer (FRET) labels, and
(b) a fluorophore and a quencher.

20. The method of claim 1, wherein the method utilizes a probe to detect a single nucleotide polymorphism (SNP) in the target nucleic acid.

* * * * *

UNITED STATES PATENT AND TRADEMARK OFFICE
CERTIFICATE OF CORRECTION

PATENT NO. : 11,685,957 B2
APPLICATION NO. : 17/199683
DATED : June 27, 2023
INVENTOR(S) : Higgins et al.

It is certified that error appears in the above-identified patent and that said Letters Patent is hereby corrected as shown below:

On the Title Page

| Column | Line | |
|---|---|---|
| 1 | "Related U.S. Application Data" | change "(60)" to -- (63) -- |

In the Specification

| Column | Line | |
|---|---|---|
| 1 | 6 | change "continuation" to -- continuation of -- |
| 4 | 39 | change "(TMPT)," to -- (TPMT), -- |
| 6 | 15-16 | change "deoxygaunosine" to -- deoxyguanosine -- |
| 9 | 64 | change "the a" to -- a -- |
| 18 | 22 | change "fluorescence energy transfer (FRET)" to -- fluorescence resonance energy transfer (FRET) -- |

In the Claims

| Column | Line | |
|---|---|---|
| 25 | 6 | change "whereby" to -- whereby: -- |
| 25 | 24 | change "detect to" to -- detect -- |
| 26 | 46 | change "consisting of" to -- consisting of: -- |

Signed and Sealed this
Fifth Day of September, 2023

Katherine Kelly Vidal
*Director of the United States Patent and Trademark Office*